United States Patent [19]
Abram et al.

[11] Patent Number: 5,872,280
[45] Date of Patent: Feb. 16, 1999

[54] LEUKOTRIENE ANTAGONISTIC BENZOIC ACID DERIVATIVES

[75] Inventors: Trevor Smyth Abram, Marlow Bucks; Nigel James Cuthbert, Bucks; Hilary Patricia Francis, Berks; Phillip John Gardiner, High Wycombe Bucks; Peter Norman, Bucks; Stephen Richard Tudhope, Berks, all of Great Britain

[73] Assignee: Bayer Aktiengesellschaft, Leverkusen, Germany

[21] Appl. No.: 748,331

[22] Filed: Nov. 13, 1996

[30] Foreign Application Priority Data

Nov. 23, 1995 [GB] United Kingdom .................... 9523946

[51] Int. Cl.$^6$ .................................................. C07C 315/00
[52] U.S. Cl. .......................... 562/430; 562/444; 562/455; 564/84; 564/85; 564/88; 514/562; 514/563
[58] Field of Search ...................................... 562/430, 444, 562/455; 564/84, 85, 88; 514/562, 563

[56] References Cited

U.S. PATENT DOCUMENTS 5,221,760  6/1993  Rosentreter et al. .
5,246,966  9/1993  Meier et al. .

FOREIGN PATENT DOCUMENTS

WO/24442  9/1993  WIPO .

OTHER PUBLICATIONS

Tudhope et al., Eur.J.Pharmacol. (1994) 246, 317–323.

*Primary Examiner*—Paul J. Killos
*Attorney, Agent, or Firm*—Sprung Kramer Schaefer & Briscoe

[57] ABSTRACT

The invention relates to benzoic acid derivatives being leukotriene antagonists. The compounds therefore are suitable as active ingredients in medicaments particularly in medicaments for the treatment of respiratory diseases.

12 Claims, No Drawings

LEUKOTRIENE ANTAGONISTIC BENZOIC ACID DERIVATIVES

The present invention refers to leukotriene antagonistic benzoic acid derivatives, a process for their preparation and their use in medicaments for the prevention and treatment of acute and chronic inflammatory processes, particularly of the respiratory tract.

Leukotrienes are important mediators in a number of pathological disease states. Accordingly, compounds blocking their actions, leukotriene antagonists, provide a useful therapy for the treatment of a variety of respiratory and circulatory disorders in which leukotrienes are involved. This invention relates to benzoic acid derivatives which are leukotriene antagonists and therefore useful in the treatment of asthma and other airway diseases.

The physiological effects of sulfidopeptide-leukotrienes are mediated by two distinct receptor types. However, in Compound A an antagonist has been identified that, in contrast to other leukotriene antagonists, had comparable activity at both receptor types (Tudhope et al., Eur. J. Pharmacol. (1994) 264, 317–323). It has been described alkenoic acid derivatives of Compound A, that display enhanced activity at one receptor type (cys-LT1), in EP 341,551 and EP 494,621. However, like the prototype structure these compounds also contained a chiral centre.

Compound A

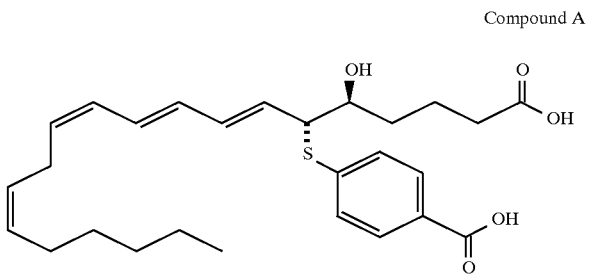

The invention relates to leukotriene antagonistic benzoic acid derivatives of the formula (I)

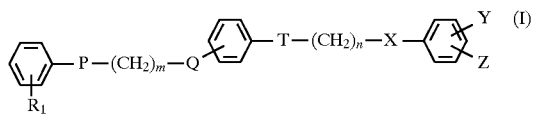

where
$R^1$ represents hydrogen, alkyl having up to 6 carbon atoms or represents substituted phenyl,
P and Q each represent oxygen, sulfur or a bond,
X represents oxygen, sulfur or —CONH—,
T represents an ethylene group, oxygen, sulfur or a bond,
Y represents a group —COOH, —NHSO$_2$R$^3$ or —CONHSO$_2$R$^3$
wherein
  $R^2$ denotes hydrogen, halogen, trifluoromethyl, trifluoromethoxy, nitro, cyano or denotes alkyl or alkoxy,
and
  Z represents a group of the formula —COOH, COR$^4$, —CO(CH$_2$)$_p$CO$_2$H, —O(CH$_2$)$_p$CO$_2$H, —S(CH$_2$)$_p$CO$_2$H, NO$_2$, —CONHWCO$_2$H or —NHWCO$_2$H
wherein
  $R^2$ has the above mentioned meaning,
  $R^3$ denotes trifluoromethyl, alkyl or optionally substituted phenyl, $R^4$ represents a group of the formula WCO$_2$H or alkyl,
p is an integer from 0 to 5 and
W denotes phenylene, an alkylene group having up to 8 carbon atoms, which is optionally substituted by alkyl or cycloalkyl each having up to 6 carbon atoms or denotes a group —CO(CH$_2$)$_q$ or —(CH$_2$)$_q$—
where
  q is an integer from 0 to 5,
  m is an integer from 0 to 6
and
  n is an integer from 0 to 4
and salts thereof.

Benzoic acid derivatives of formula (I) lack a chiral centre but, display activity as leukotriene antagonists on cys-LT1receptors. Furthermore, these compounds surprisingly have activity on cys-LT2 receptors comparable to, or better than Compound A.

The compounds according to the invention bearing an acidic function can also exist in form of their salts. In general, the salts which may be mentioned in this context are those with organic or inorganic bases.

Physiologically acceptable salts are preferred within the scope of the present invention. Examples of such salts are those derived from ammonium hydroxide and alkali earth metal hydroxides, carbonates and bicarbonates, as well as salts derived from aliphatic and aromatic amines, aliphatic diamines and hydroxy alkylamines. Bases for example useful in the preparation of such salts include ammonium, sodium or potassium hydroxide, sodium or potassium carbonate and bi-carbonate, calcium hydroxide, methylamine, diethylamine, ethylene diamine, tri-ethylamine, cyclohexylamine and ethanolamine.

Particularly preferred are the potassium and sodium salts of the compounds according to the invention. But it is to be understood that other, non-pharmaceutical salts are included in the invention since they may be useful for identification, characterization or purification of the compounds.

Preferred are compounds of formula I wherein
  $R^1$ represents hydrogen,
  P and Q represent oxygen,
  X represents oxygen sulfur or —NH—,
  T represents a bond,
  Y represents a group —COOH and/or
  Z has the abovementioned meaning
  m represents an integer H
and their salts.

Particularly preferred leukotriene antagonistic benzoic acid derivatives of the formula (Ia) are represented by the general formula (II) where the meanings of X, Z and n are as defined above. Such compounds display enhanced leukotriene antagonist activity.

(Ia)

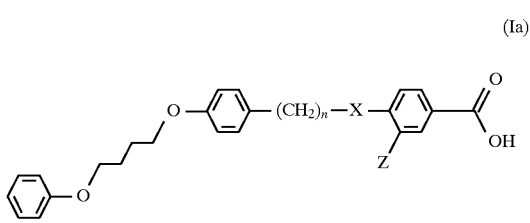

An especially preferred embodiment of the invention is represented by compounds of the formula (I), wherein
  $R^1$ represents hydrogen,
  P and Q represent oxygen, T represents a bond, X represents oxygen, Y represents a group —COOH, m is an integer 4, n is an integer 3 and z represents a group —CONH(CH$_2$)$_q$CO$_2$H, —NHCO(CH$_2$)$_q$CO$_2$H or —CONHC$_6$H$_4$CO$_2$H where q is an integer 0 to 5 and salts thereof.

Very particularly preferred are:

3-aza-4-(5-carboxy-2-[3-{4-phenoxybutoxy}phenyl-propoxy]-4-oxobutanoic acid, 4-aza-5-(5-carboxy-2-[3-{4-phenoxybutoxy}phenyl-propoxy]-5-oxopentanoic acid, 5-aza-6-(5-carboxy-2-[3-{4-phenoxybutoxy}phenyl-propoxy]-6-oxohexanoic acid, 5-aza-5-(5-carboxy-2-[2-{4-phenoxybutoxy}phenyl-ethoxy]-6-oxohexanoic acid, 6-aza-6-(5-carboxy-2-[3-{4-phenoxybutoxy}phenyl-propoxy]-4-oxoheptanoic acid, N-(2-carboxyphenyl)-2-[3-{4-phenoxybutoxy}phenyl-propoxy]-5-carboxybenzamide, N-(3-carboxyphenyl)-2-[3-{4-phenoxybutoxy}phenyl-propoxy]-5-carboxybenzamide, N-(4-carboxyphenyl)-2-[3-{4-phenoxybutoxy}phenyl-propoxy]-5-carboxybenzamide, 4-aza-3-(5-carboxy-2-[3-{4-phenoxybutoxy}phenyl-propoxy]-3-oxobutanoic acid, 5-aza-4-(5-carboxy-2-[3-{4-phenoxybutoxy}phenyl-propoxy]-4-oxopentanoic acid, 6-aza-6-(5-carboxy-2-[3-{4-phenoxybutoxy}phenyl-propoxy]-5-oxohexanoic acid, 7-aza-7-(5-carboxy-2-[3-{4-phenoxybutoxy}phenyl-propoxy]-3-oxoheptanoic acid.

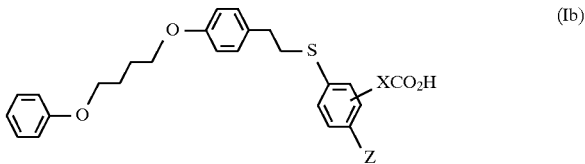

(Ib)

Another preferred embodiment of the invention is illustrated by structures of the formula (Ib), where X represents CONH(CH$_2$)$_q$, NHCO(CH$_2$)$_q$ or O(CH$_2$)$_q$ and Z represents carboxylic acid, NHSO$_2$R$^2$ or CONHSO$_2$R$^2$, where R$_2$ represents C$_1$–C$_4$-alkyl or phenyl, and q is an integer 1 to 5 and salts thereof.

Specific examples of this include the following:

5-aza-5-(5-carboxy-2-(3-[4-{4-phenoxybutoxy}phenyl]-1-thiapropyl)phenyl)-4-oxopentanoic acid, 6-aza-6-(5-carboxy-2-(3-[4-{4-phenoxybutoxy}phenyl]-1-thiapropyl)phenyl)-5-oxohexanoic acid, 5-aza-5-(5-[methylsulfonylamino]-2-(3-[4-{4-phenoxybutoxy}phenyl]-1-thiapropyl)-phenyl)-4-oxopentanoic acid.

3-([4-carboxy-1-oxobutyl)-4-(3-[4-{4-phenoxybutoxy}-phenyl]-1-thiapropyl) phenyl)-N-phenylsulfonylbenz-amide.

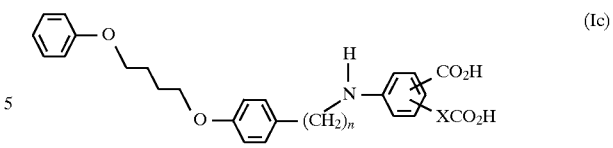

(Ic)

Another preferred form of the invention is illustrated by structures of the formula (Ic), where n is 2 or 3 and X represents (CH$_2$)$_q$, S(CH$_2$)$_q$ or CO(CH$_2$)$_q$, and q is an integer 0 to 5 and salts thereof.

Specific examples of this include the following:

5-carboxy-2-[([3-{4-phenoxybutoxy}phenyl]-1-oxopropyl)amino]phenylacetic acid, 5-carboxy-2-[([3-{4-phenoxybutoxy}phenyl]-1-oxopropyl)amino]phenoxyacetic acid, 5-carboxy-2-[([3-{4-phenoxybutoxy}phenyl]-1-oxopropyl)amino]phenoxybutanoic acid, 5-carboxy-2-[([3-{4-phenoxybutoxy}phenyl]-1-oxopropyl)amino]phenoxyhexanoic acid, 5-carboxy-2-[([3-{4-phenoxybutoxy}phenyl]-1-oxopropyl)amino]phenyl-5-thiapentanoic acid, 5-carboxy-2-[([3-{4-phenoxybutoxy}phenyl]-1-oxopropyl)amino]phenyl-4-oxapentanoic acid.

Additionally a process for the preparation of the compounds of formula (I) has been found characterized in that compounds of the formula (II)

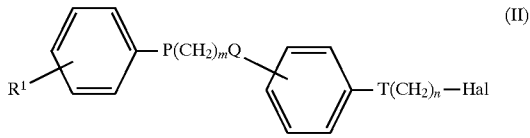

(II)

wherein

Hal denotes chlorine, bromine or iodine are reacted in the presence of an inert solvent, optionally in the presence of a base with compounds of the formula

(III)

and optionally the functional groups Y and Z are transformed by methods known in the art.

Halide anions are preferably chlorides, bromides or iodides.

Suitable inert solvents for the process (variant A) according to the invention are those conventional organic solvents which do not change under the reaction conditions. They preferably include ethers such as diethyl ether, butyl methyl ether, dioxane, tetrahydrofuran, glycol dimethyl ether or diethylene glycol dimethyl ether, or hydrocarbons such as benzene, toluene, xylene or petroleum fractions, or amides such as dimethylformamide or hexamethylphosphoric triamide, or 1,3-dimethyl-imidazolidin-2-one, 1,3-dimethyltetrahydro-pyrimidin-2-one or dimethyl sulphoxide. It is likewise possible to use mixtures of the solvents mentioned.

Suitable bases are the conventional basic compounds for basic reactions. These preferably include alkali metal hydrides such as, for example, sodium hydride or potassium hydride, or alkali metal alcoholates such as sodium methanolate, sodium ethanolate, potassium methanolate, potassium ethanolate or potassium tert.-butylate, or amides such as sodium amide or lithium diisopropylamide, or organolithium compounds such as phenyllithium, butyllithium or methyllithium or sodium hexamethyldisilazane or potassium hexamethyldisilazane.

The choice of solvent of base depends on the stability, sensitivity to hydrolysis or CH acidity of the respective phosphorus compound. Ethers such as diethyl ether, tetrahydrofuran, dimethoxyethane or dioxane, together with a co-solvent such as dimethylformamide or 1,3-dimethyltetrahydropyrimidin-2-one or 1,3-dimethylimidazolid-2-one, are particularly preferably used as solvent. Alkali metal alcoholates such as potassium tert.-butylate, or organolithium compounds such as phenyllithium or butyllithium or sodium hydride are particularly preferably used as bases.

The reaction is generally carried out in the temperature range from $-80°$ C. to $+70°$ C., preferably from $-80°$ C. to $+20°$ C.

The reaction may be carried out at atmospheric, elevated or reduced pressure (for example 0.5 to 5 bar). In general, the reaction is carried out at atmospheric pressure.

The variation of the functional group can be achieved by hydrolysis, esterification, amidation etc. which are well known to those skilled in the art.

Generally, the inventive compounds can be prepared according to the following general scheme:

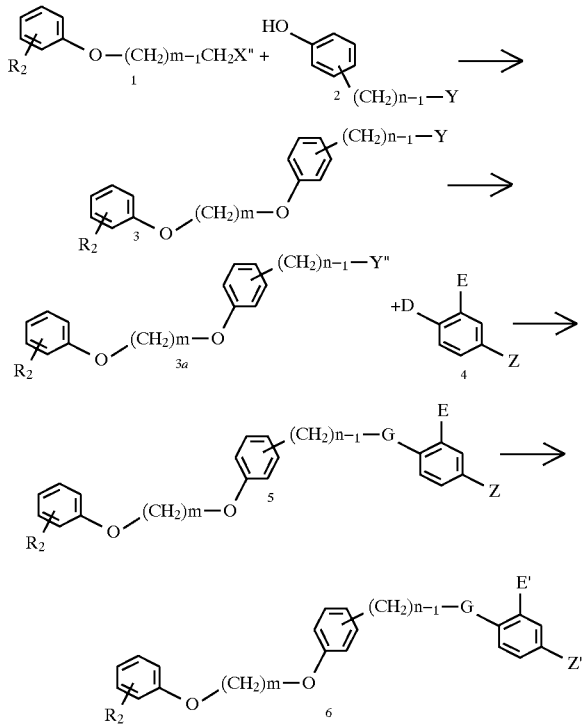

Where $R_2$=H, halogen, $CF_3$, $CF_3O$, $NO_2$, CN, alkoxy or alkyl
W=a bond, alkylene or phenylene
m is an integer from 0 to 6
n is an integer from 0 to 4
R' and R" are each H or lower alkyl
R''' is alkyl, optionally substituted phenyl or $CF_3$ Step 1 Lipophilic Tail
  X"=Br, Cl, I or Otosylate; Y=OH or $CO_2H$
  A phenoxyalkylene derivative (1) is coupled with a substituted phenol (2) under basic conditions. (As described in step a) of Scheme A)

Step 2 Leaving Group Modification
  Y"=Br, Cl, I or S(NH)NH$_2$
  For (3) Y=OH the hydroxyl group is converted into an appropriate group in one, or two steps, for coupling with a trisubstituted benzene ring to give (3a). (As described in steps b) & c) of Scheme A)

Step 3 Addition of the 'Head Group'
  D=Cl, OH or NH$_2$; Z=CO$_2$R' or NO$_2$; G=O, S or CONH
  E=CONHWCO$_2$R", NHCOWCO$_2$R", WCO$_2$R", COWCO$_2$R", OWCO$_2$R", SWCO$_2$R" or NO$_2$
  The lipophilic tail (3) or (3a) is condensed with a trisubstituted benzene (4).
  a) The tail portion (3, Y=CO2H) is coupled with an appropriately substituted aniline (4, D=NH2) as described in Scheme E.
  b) A halide (3a) is condensed with a phenol (4, D=OH) under basic conditions as described in part b of Schemes B & C or part a of Scheme D.
  c) A thiourea (3a) is coupled with a o-chloronitrobenzene (4, D=Cl, E=NO$_2$) as described in part a of Scheme F.

Step 4 Functional Group Modification
  If E=NO$_2$ then E'=NH$_2$, NHCOWCO$_2$R" or NHSO$_2$R'''
  otherwise
  E'=E
  Z'=CO$_2$R', CONHSO$_2$R''' or NHSO$_2$R'''
  After formation of the link (G) either, or both, of the groups D and E are modified to give the desired substituents in one or more steps.
  If E or Z=NO$_2$ it is reduced as described in part b of Scheme D. The amine is then condensed with either the acid or acid chloride forms of either a carboxylic acid or a sulfonic acid.
  Basic hydrolysis of the esters (6, R' and/or R"=alkyl) yields the corresponding carboxylic acids.

Additionally the compounds according to the invention can be prepared as described as follows:

Scheme A

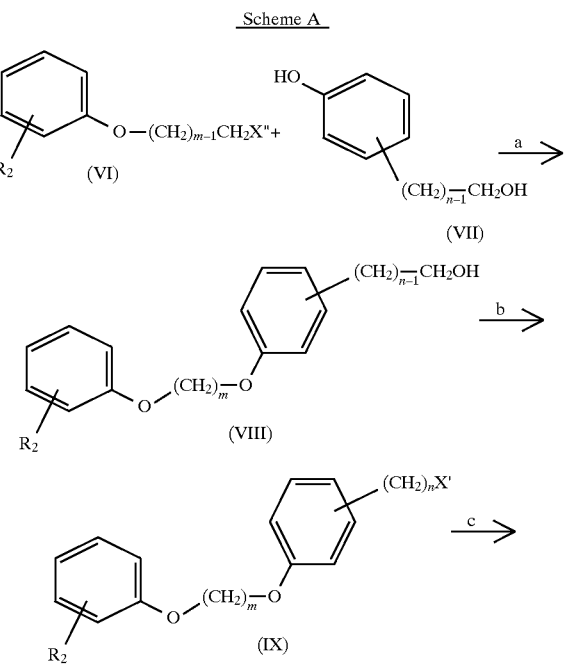

-continued
Scheme A

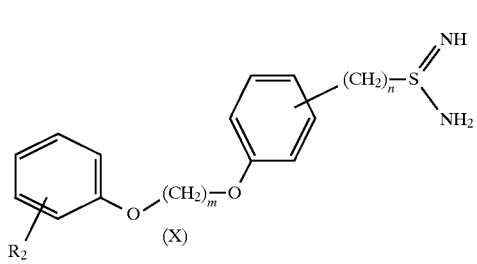

The general procedure employed in the preparation of the lipophilic portion of the majority of the compounds of the invention is illustrated in Scheme A. The first two steps are generally applicable for the preparation of compounds of the formula (I). The third step shown is only applicable in the preparation of compounds of the formula (V).

In step a) phenoxyalkylhalides, or phenoxyalkyltosylates, (VI) are reacted with phenols (VII) in an inert solvent in the presence of a base. Suitable reagents for effecting this transformation are alkali metal carbonates, with dimethylformamide being preferred as the solvent. Such reactions are preferably performed at temperatures between 20° C. and 150° C.

In step b) the primary alcohol (VIII) is converted to a halide (IX). Many reagents for effecting this transformation are known to those skilled in the art. Preferred forms of (IX) are those in which X is bromide or iodide. Conversion to iodides is effected by reaction of the alcohol with activated iodides, reaction with phosphorus bromides or by generation of activated bromides as may be achieved with carbon tetrabromide and triphenylphosphine.

In step c) reaction of the halide (IX) with thiourea in a suitable solvent provides the thioureas (X). Such reactions are preferably performed at temperatures between 20° C. and 150° C. and in polar solvents such as acetone.

Scheme B

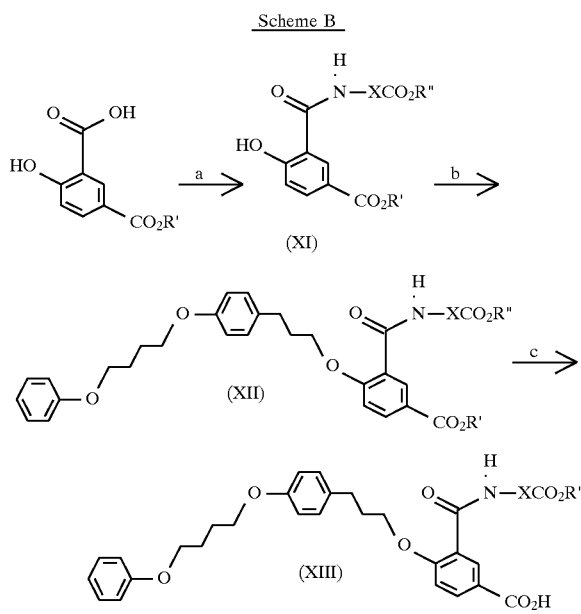

a) ACOXCO$_2$R"
b) (IX)
c) base

-continued
Scheme B

A) H$_2$NXCO$_2$R"
b) (IX)
c) base

The structure (XIII) denotes one preferred form of compounds of the formula (III), where X represents CONH(CH$_2$)$_q$CO$_2$H. The preparation of such compounds is illustrated in scheme B.

Monoesters of 4-hydroxy-isophthalic acid are coupled with ω-aminoalkylesters to give the amides (XI). Such steps are best performed in an inert solvent and utilise a suitable agent for the activation of the carboxylic acid group. Preferred activating agents are carbonyl di-imidazole and phosphinic chlorides, suitable solvents are tetrahydrofuran or dimethylformamide. Alkylation of the amide is then effected by reaction with alkyl halides (IX) in an inert solvent in the presence of a base. Suitable reagents for effecting this transformation are alkali metal carbonates, with dimethylformamide being preferred as the solvent. Such reactions are preferably performed at temperatures between 20° C. and 150° C. Hydrolysis of the diester (XII) is effected by treatment with aqueous base. Such hydrolysis are performed in the presence of organic co-solvents such as tetrahydrofuran or alcohol. Suitable bases are alkali metal hydroxides, especially lithium hydroxide. These reactions are preferably performed at temperatures between 20° C. and 100° C. Room temperature is a particularly suitable temperature at which to perform these reactions.

Scheme C

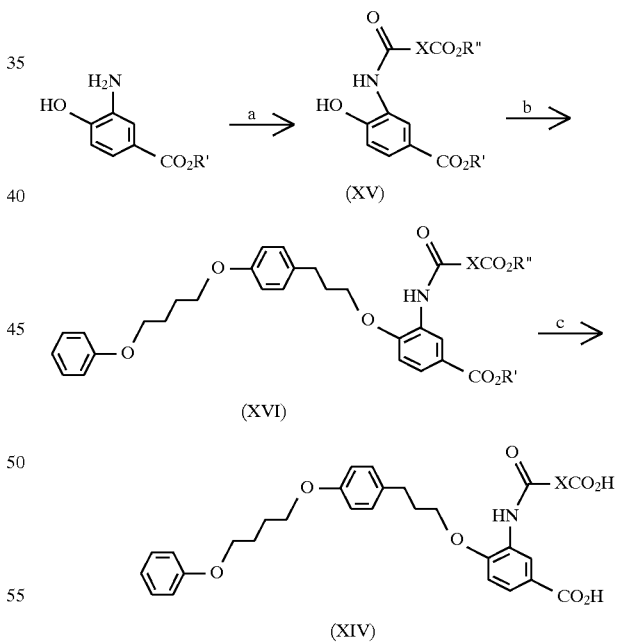

Another preferred form of (III) is that described by the formula (XIV). One method of preparation of (XIV) is shown in Scheme C, which is directly analogous to Scheme B. Esters of 3-amino-4-hydroxybenzoate are coupled with monoesters of ω-dicarboxylic acids to give the amides (XV). Such steps are best performed in an inert solvent and utilise a suitable agent for the activation of the carboxylic acid group. Preferred activating agents are carbonyl di-imidazole and phosphinic chlorides, suitable solvents are tetrahydrofuran or dimethylformamide. Alkylation of the amide (XV) is then effected by reaction with alkyl halides (IX) in an inert solvent in the presence of a base. Suitable reagents for effecting this transformation are alkali metal carbonates, with dimethylformamide being preferred as the solvent. Such reactions are preferably performed at temperatures between 20° C. and 150° C. Hydrolysis of the diester (XVI) is effected by treatment with aqueous base. Such hydrolyses are best performed in the presence of organic co-solvents such as tetrahydrofuran or alcohol. Suitable basis are alkali metal hydroxides, especially lithium hydroxide. These reactions are preferably performed at temperatures between 20° C. and 100° C. Room temperature is a particularly suitable temperature at which to perform these reactions.

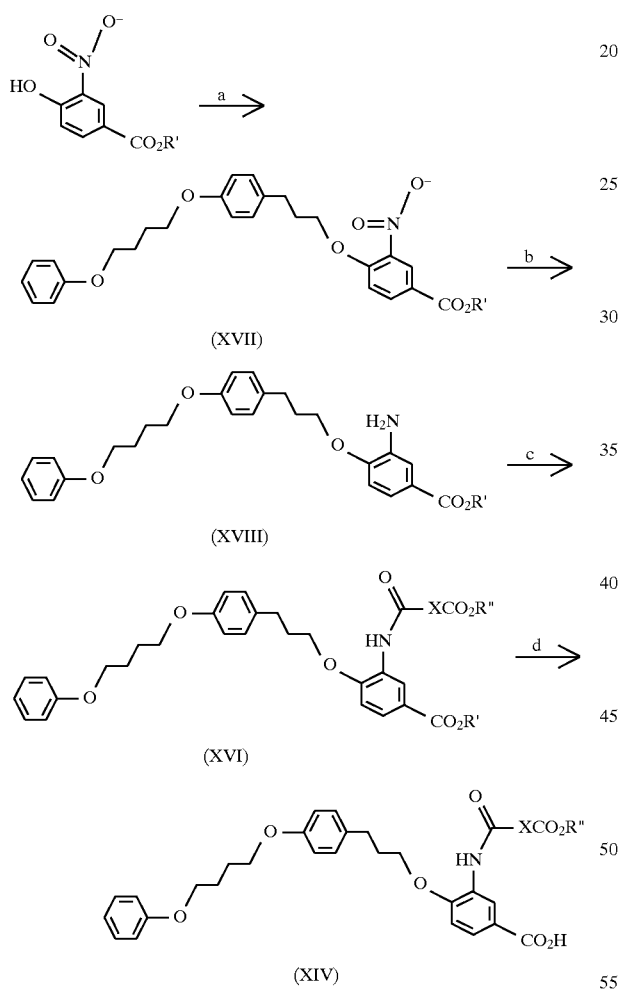

a) (IX)
b) $H_2$
c) $AOCXCO_2R''$
d) base

A preferred means of preparation of compounds of the formula (XIV) is illustrated in Scheme D. Alkylation of 4-hydroxy-3-nitrobenzoate esters to give the nitro ester (XVII) is followed by reduction of the nitrogroup to give the amine (XVIII). This is then converted to the amide (XVI) using the conditions employed in Scheme C.

Alkylation of the nitro benzoate is effected by reaction with alkyl halides (IX) in an inert solvent in the presence of a base. Suitable reagents for effecting this transformation are alkali metal carbonates, with dimethylformamide being preferred as the solvent. Such reactions are preferably performed at temperatures between 20° C. and 150° C. Reduction of the nitrobenzene to an aniline may be achieved using a variety of conditions known to one skilled in the art. Suitable reagents for effecting this transformation are hydrogen, in the presence of a catalyst, or certain metal cations. A preferred reagent is tin(II)chloride in an alcoholic solvent. Such reactions are preferably performed at temperatures between 50° C. and 100° C. Acylation of the amine (XVIII) is performed by reaction with an activated carboxylic acid. Such steps are best performed in an inert solvent and utilise a suitable agent for the activation of the carboxylic acid group. Preferred activating agents are carbonyl diimidazole and phosphinic chlorides, suitable solvents are tetrahydrofuran or dimethylformamide. Hydrolysis of the diester (XVI) is effected by treatment with aqueous base. Such hydrolyses are best performed in the presence of organic co-solvents such as tetrahydrofuran or alcohol. Suitable bases are alkali metal hydroxides, especially lithium hydroxide. These reactions are preferably performed at temperatures between 20° C. and 100° C. Room temperature is a particularly suitable temperature at which to perform these reactions.

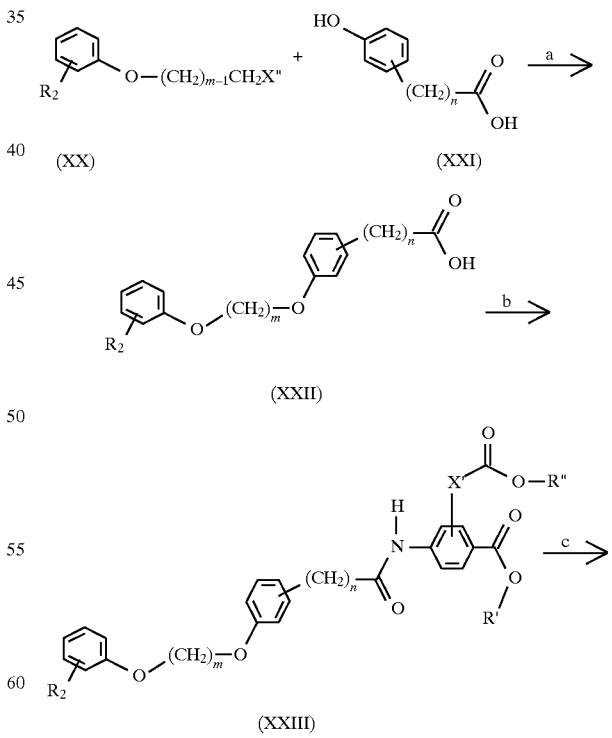

-continued
Scheme E

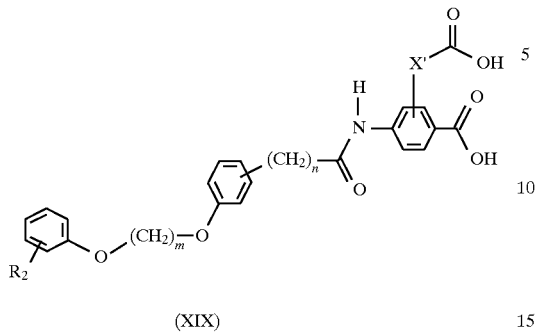

(XIX)

a) base
b) ArNH$_2$
c) base

Another preferred form of compounds of the general formula (I) is denoted by amide derivatives of the formula (XIX). A preferred process for their preparation is illustrated in Scheme E. Alkylation of (hydroxphenyl)alkanoic acids (XXI) by phenoxyalkyl halides (XX) gives alkanoic acid derivatives (XXI). These are then condensed with suitably substituted anilines to give the amides (XXIII), ester hydrolysis then furnishes the dicarboxylic acids (XIX).

Alkylation of the acids (XXI) is effected by reaction with alkyl halides (XX) in an inert solvent in the presence of a base. Suitable reagents for effecting this transformation are alkali metal carbonates, with dimethylformamide being preferred as the solvent. Such reactions are preferably performed at temperatures between 20° C. and 150° C. The carboxyl group is then activated prior to addition of the aniline. Preferred activating agents are carbonyl di-imidazole and phosphinic chlorides, suitable solvents are tetrahydrofuran or dimethylformamide. Alternatively the acid is activated by conversion to the acid chloride by reaction with a suitable halogenating agent. Preferred reagents are thionyl chloride and oxalyl chloride. Such reactions are preferentially performed in chlorinated solvents at temperatures between 20° C. and 100° C. Hydrolysis of the diester (XXIII) is effected by treatment with aqueous base. Such hydrolyses are best performed in the presence of organic co-solvents such as tetrahydrofuran or alcohol. Suitable bases are alkali metal hydroxides, especially lithium hydroxide. These reactions are preferably performed at temperatures between 20° C. and 100° C. Room temperature is a particularly suitable temperature at which to perform these reactions.

Scheme F (XXIV)

-continued
Scheme F (XXV)

(XXVI)

(XXVII)

(XXIII)

a) NaOH
b) SnCl$_2$
c) ACO(CH$_2$)$_p$CO$_2$R"
d) base

Another preferred form of the invention is illustrated by thioethers of the general formula (XXIII). A process for their preparation is illustrated in Scheme F. In the presence of a strong base thioureas (XXIV) will effect nucleophilic substitution of nitrobenzenes. Suitable bases are alkali metal hydroxides, preferably sodium hydroxide. Such reactions are preferably performed in the presence of an organic co-solvent; suitable solvents are lower alcohols. These reactions are preferably performed at temperatures between 20° C. and 100° C. Temperatures between 80° C. and 100° C. are particularly suitable temperatures at which to perform these reactions. The presence of the sulfur atom reduces the choice of reagents for the reduction of the nitrobenzene (XXV) to the aniline (XXVI). A preferred reagent is tin(II)chloride in an alcoholic solvent. Such reactions are preferably performed at temperatures between 50° C. and 100° C. Acylation of the amine (XXVI) is performed by reaction with an activated carboxylic acid. Such steps are best performed in an inert solvent and utilise a suitable agent for the activation of the carboxylic acid group. Preferred activating agents are carbonyl di-imidazole and phosphinic chlorides, suitable solvents are tetrahydrofuran or dimethylformamide. Hydrolysis of the ester (XXVII) is effected by treatment with aqueous base. Such hydrolyses are best performed in the presence of organic co-solvents such as tetrahydrofuran or alcohol. Suitable bases are alkali metal hydroxides, especially lithium hydroxide. These reactions are preferably performed at temperatures between 20° C. and 100° C. Room temperature is a particularly suitable temperature at which to perform these reactions.

Test Methods

The compounds of the invention were shown to be effective as leukotriene antagonists on both cys-LT1 and cys-LT2 receptor systems. The representative preparations used to evaluate these compounds were the inhibition of $^3H$-$LTD_4$ binding to guinea-pig lung membranes, as described in EP 494621, and the inhibition of both $LTD_4$-induced and $LTC_4$-induced contractions of guinea-pig tracheae as described by Tudhope et al., Eur. J. Pharmacol (1994) 264, 317–323. The results obtained in these tests are shown in Tables 1 to 3, respectively.

TABLE 1

$pK_i$ values for the inhibition of $^3H$-$LTD_4$ binding to guinea-pig lung membranes

| Example No. | $pK_i$ |
| --- | --- |
| 4 | 6.1 |
| 5 | 6.4 |
| 6 | 6.6 |
| 7 | 5.7 |
| 11 | 5.8 |
| 12 | 6.0 |
| 13 | 6.0 |
| 14 | 6.5 |
| 15 | 5.3 |
| 16 | 7.3 |
| 17 | 6.4 |
| 18 | 6.2 |
| 22 | 6.6 |
| 23 | 5.5 |
| 24 | 6.3 |
| 25 | 5.8 |
| 27 | 4.9 |
| 29 | 5.7 |
| 30 | 5.3 |
| 31 | 6.5 |
| 34 | 5.7 |
| 35 | 5.8 |
| 36 | 4.6 |

TABLE 2

$pK_B$ values for the inhibition of $LTD_4$-induced contractions of guinea-pig trachea.

| Example No. | $pK_B$ |
| --- | --- |
| 4 | 6.9 |
| 5 | 7.1 |
| 6 | 7.1 |
| 7 | 6.6 |
| 8 | 6.2 |
| 9 | 6.4 |
| 10 | 6.5 |
| 11 | 6.6 |
| 12 | 6.6 |
| 13 | 6.9 |
| 14 | 6.6 |
| 15 | 6.4 |
| 16 | 7.3 |
| 17 | 6.6 |
| 18 | 7.1 |
| 19 | 6.3 |
| 20 | 6.5 |
| 21 | 7.5 |
| 22 | 7.3 |
| 23 | 5.9 |
| 24 | 7.3 |
| 25 | 5.8 |
| 26 | 5.9 |
| 27 | 5.0 |
| 29 | 5.7 |
| 30 | 4.7 |
| 31 | 5.4 |
| 32 | 6.5 |
| 33 | 6.6 |
| 34 | 5.6 |
| 35 | 6.2 |

TABLE 3

$pK_B$ values for the inhibition of $LTC_4$-induced contractions of guinea-pig trachea.

| Example No. | $pK_B$ |
| --- | --- |
| 4 | 7.2 |
| 5 | 5.9 |
| 6 | 7.1 |
| 10 | 6.9 |
| 11 | 6.0 |
| 12 | 6.3 |

EXAMPLES

All $^1H$-NMR were performed at 60 MHz using the solvent indicated and tetramethylsilane as an internal standard. All HPLC data were obtained using a 25×4 mm Lichrosorb RP-18 column with 7 µm packing. The eluent was a mixture of acetonitrile:water:acetic acid, buffered to pH 5.6 in the indicated proportions, at a flow rate of 1 ml/min.

Example 1 a) 3-(4-[4-phenoxybutoxyl]phenyl)-1-propanol

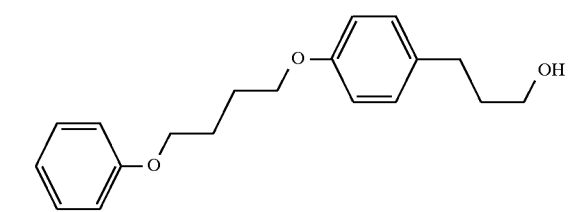

4-Phenoxybutylbromide (34.2 g), 3-(4-hydroxyphenyl)-1-propanol (25 g) and potassium carbonate (20.6 g) were stirred for 24 h at 60° C. in dimethylformamide (140 ml). After cooling, pouring into water gave a white precipitate which was washed with water and recrystallised from chloroform to give the title compound as a white solid (16.9 g) m.p. 98°–99° C.

$^1H$-NMR ($CDCl_3$) δ: 1.8–2.3(6H,m), 2.60 (2H,t), 3.60 (2H,t), 3.8–4.2 (4H,m), 6.6–7.5 (9H,m).

b) 1-iodo-3-[4-(4-phenoxybutoxy)phenylpropane

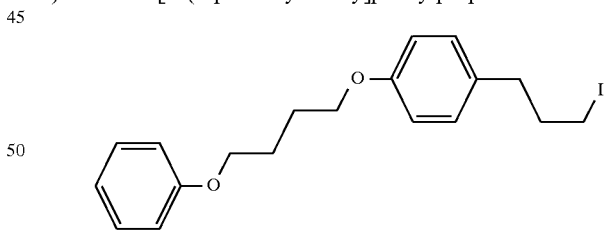

The product of Example 1a (10 g) and triphenylphosphine (9.6 g) were dissolved in anhydrous benzene (100 ml). A solution of diethyl azodicarboxylate (6 ml) in benzene (15 ml) was added over 5 minutes. Iodomethane (2.5 ml) in benzene (10 ml) was then added and stirred for 2 hours. This mixture was concentrated in vacuo and the crude product flash chromatographed on silica in 50% diethyl ether-hexane. Column chromatography on alumina with 20% diethyl ether-hexane then dichloromethane gave product that was crystallised from diethyl ether-hexane to give a solid m.p. 76°–77° C., 3.7 g.

$^1H$-NMR ($CDCl_3$) δ: 1.7–2.3 (6H,m), 2.60 (2H,t), 3.10 (2H,t), 3.8–4.1 (4H,m), 6.7–7.5 (9H,m).

c) 1-bromo-3-[4-(4-phenoxybutoxy]phenylpropane

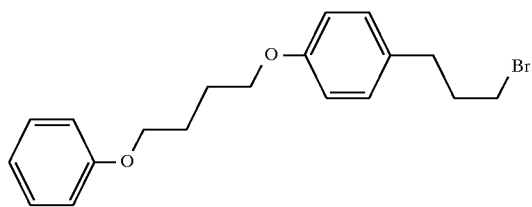

The product of Example 1a (10 g), N-bromosuccinimide (12.5 g) were dissolved in dichloromethane (85 ml) and triphenylphosphine (9.6 g) was slowly added at 0° C. The solution was stirred for 1 h then concentrated and eluted through silica with 50% ether in pentane to give a white solid (11.6 g) m.p. 74°–75° C.
$^1$H-NMR (CDCl$_3$) δ: 1.7–2.0 (4H,m), 2.15 (2H,t), 2.65 (2H,t), 3.3 (2H,t), 3.8–4.1 (4H,m), 6.7–7.5 (9H,m).
Following the procedure of Example 1a were also prepared:

3-(3-[4-phenoxybutoxy]phenyl)propanol and 2-(4-[4-phenoxybutoxy]phenyl)-ethanol
Following the procedure of Example 1b were also prepared:

1-iodo-3-(3-[4-phenoxybutoxy]phenyl)propane and
1-iodo-2-(4-[4-phenoxybutoxy]phenyl)ethane
Following the procedure of Example 1c were also prepared:

1-bromo-3-(3-[4-phenoxybutoxy]phenyl)propane
and 1-bromo-2-(4-[4-phenoxybutoxyl]phenyl)ethane Example 2

2-(4-[4-phenoxybutoxy]phenyl)ethylthiourea

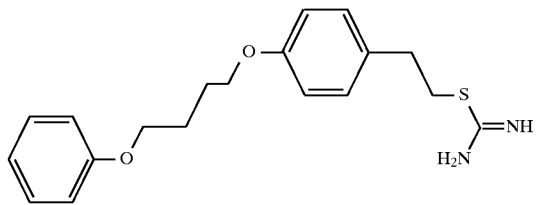

1-bromo-3-[4-(4-phenoxybutoxy]phenylpropane (3.8 g) and thiourea (0.8 g) were refluxed for 20 h in ethanol (80 ml). On cooling this deposited the hydrobromide salt of the thiourea as a white powder (3.2 g) m.p. 119°–120° C.

Example 3

3-(4-[4-phenoxybutoxy]phenyl)propanoic acid
a) Methyl 3-(4-hydroxyphenyl)propionate

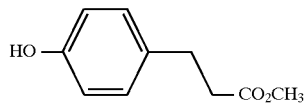

3-(4-Hydroxyphenyl)propionic acid (50 g) was added to 3% hydrogen chloride in methanol (500 ml) and refluxed for 2.5 h. The solution was concentrated in vacuo then diluted with ethyl acetate and neutralised with sodium bicarbonate. The ethyl acetate extract was washed with water and saturated sodium chloride then dried and concentrated in vacuo. Vacuum distillation of the crude residue gave the product as a low melting solid m.p. 40°–41° C. (47.1 g).

b) Methyl 3-(4-[4-phenoxybutoxy]phenyl)propionate

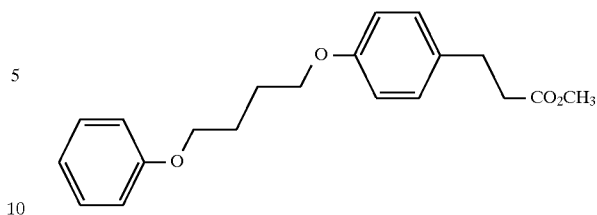

Methyl 3-(4-hydroxyphenyl)propionate (25 g), 4-phenoxybutoyl bromide (30.3 g) and potassium carbonate (73 g) were added to dry dimethylformamide (400 ml) under argon and stirred for 24 hours. The mixture was poured into ethyl acetate-water. The ethyl acetate extracts were washed with water and saturated sodium chloride then dried and concentrated in vacuo to give a solid which was recrystallised from ethyl acetate-hexane (1:4) gave the product m.p. 82°–83° C. (37.3 g).
$^1$H-NMR (CDCl$_3$) δ: 1.8–2.1 (4H,m), 2.4–3.0 (4H,m), 3.6 (3H,s), 3.8–4.2 (4H,m), 6.6–7.4 (9H,m).

c) 3-(4-[4-phenoxybutoxy]phenyl)propanoic acid

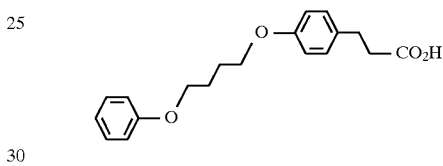

Methyl 3-(4-[4-phenoxybutoxy]phenyl)propionate (29.5 g) was added to 400 ml tetrahydrofuran—water (1:1) and lithium hydroxide monohydrate (7.5 g) added. This mixture was heated under reflux conditions for 30 minutes then allowed to cool to room temperature. Acidification with hydrochloric acid (300 ml) gave a precipitate. The precipitate was filtered off, washed with water and dried in vacuo to give the product (27.8 g) m.p. 133.0°–133.5° C.
$^1$H-NMR ([CD$_3$]$_2$CO/d$^6$-DMSO) δ: 1.8–2.2 (4H,m), 2.4–2.9 (4H,m), 3.9–4.2 (4H,m), 6.7–7.4 (9H,m).

Following the procedure of Example 3 were also prepared:
4-(4-[4-phenoxybutoxy]phenyl)butanoic acid
2-(4-[4-phenoxybutoxy]phenyl)ethanoic acid
2-(4-[4-phenoxybutoxy]phenoxy)ethanoic acid.

Example 4

5-aza-6-(5-carboxy-2-[3-{4-phenoxybutoxy}phenylpropoxy]-6-oxohexanoic acid a) N-(3-carbomethoxypropyl)-2-hydroxy-5-carbomethoxybenzamide

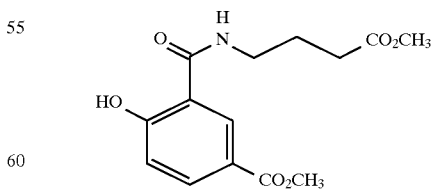

Methyl 4-aminobutanoate hydrochloride (0.8 g) and triethylamine (1.0 g) in ethyl acetate (20 ml) were added to methyl 4-hydroxyisophthalate (1 g), diphenylphosphinic chloride (1.3 g) and triethylamine (0.5 g) in ethyl acetate (30 ml). The resulting mixture was stirred for 48 h then poured into water and extracted with ethyl acetate. The product was purified by chromatography on silica gel eluting with 20% ethyl acetate in hexane to give a colourless gum (0.5 g).

$^1$H-NMR (CDCl$_3$) δ: 1.8–2.3 (2H,m), 2.45 (2H,t), 3.45 (2H,t), 3.65 (3H,s), 3.80 (3H,s), 6.96 (1H,d), 7.7 (1H,br), 8.00 (1H,dd), 8.25 (1H,d).

b) methyl 5-aza-6-(5-carbomethoxy-2-{4-phenoxybutoxy}phenylpropoxy]-6-oxohexanoate

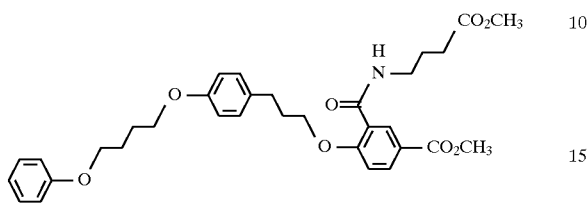

The products of Example 4a (0.1 g) and Example 1b (0.15 g) plus potassium carbonate (0.05 g) were stirred together for 18 h in dry dimethylformamide (6 ml). This was poured into water and extracted with ethyl acetate then purified by preparative TLC to give the title compound (0.1 g).

$^1$H-NMR (CDCl$_3$) δ: 1.8–2.5 (10H,m), 2.75 (2H,t), 3.45 (2H,t), 3.60 (3H,s), 3.85 (3H,s), 3.8–4.3 (6H,m), 6.7–7.4 (10H,m), 7.8 (1H,br), 8.10 (1H,d), 8.85 (1H,d).

HPLC T$_R$: 7.5 min, 80:20:0.1.

c) 5-aza-6-(5-carboxy-2-[3-{4-phenoxybutoxy}phenylpropoxy]-6-oxohexanoic acid

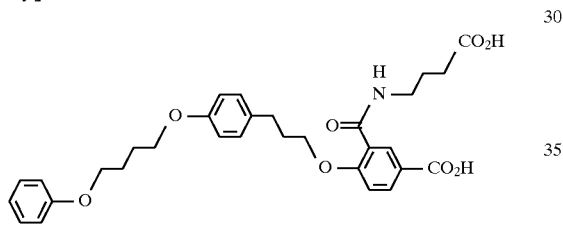

The product of Example 4b was dissolved in tetrahydrofuran (10 ml) and stirred overnight with 1M lithium hydroxide (10 ml). The tetrahydrofuran was removed at reduced pressure and the solution acidified to deposit the acid as a white solid which was collected by filtration (0.04 g). HPLC T$_R$: 3.8 min, 80:20:0.1.

Example 5

3-aza-4-(5-carboxy-2-[3-{4-phenoxybutoxy}phenylpropoxy]-4-oxobutanoic acid

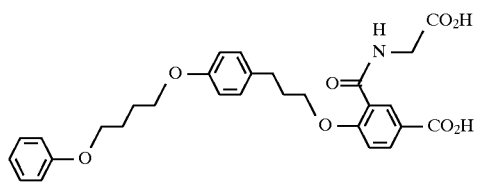

This was prepared following the procedure of Example 4 with the substitution of methyl aminoacetate for methyl 4-aminobutanoate.

HPLC T$_R$: 4.0 min, 70:30:0.1.

Ester: $^1$H-NMR (CDCl$_3$) δ: 1.8–2.2 (4H,m), 2.2 (2H,m), 2.8 (2H,t), 3.75 (3H,s), 3.85 (3H,s), 3.8–4.4 (8H,m), 6.7–7.4 (10H,m), 8.1 (1H,dd), 8.3 (1H,tr), 8.85 (1H,d)

Example 6

4-aza-5-(5-carboxy-2-[3-{4-phenoxybutoxy}phenylpropoxy]-5-oxopentanoic acid

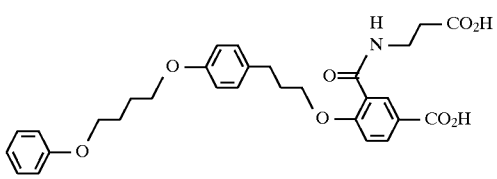

This was prepared following the procedure of Example 4 with the substitution of methyl 3-aminopropanoate for methyl 4-aminobutanoate.

HPLC T$_R$: 3.7 min, 80:20:0.1.

Ester: $^1$H-NMR (CDCl$_3$) δ: 1.8–2.1 (4H,m), 2.2 (2H,m), 2.5–3.0 (4H,m), 3.65 (3H,s), 3.85 (3H,s), 3.5–4.3 (8H,m), 6.7–7.4 (10H,m), 8.1 (1H,dd), 8.3 (1H,tr), 8.9 (1H,d).

Example 7

5-aza-6-(5-carboxy-2-[3-{4-phenoxybutoxy}phenylpropoxys]-6-oxoheptanoic acid

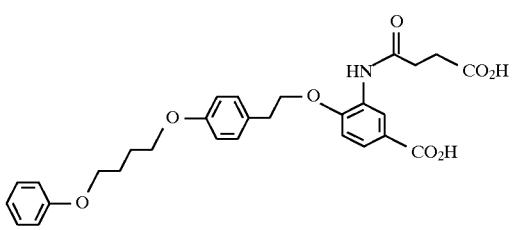

This was prepared following the procedure of Example 4 with the substitution of methyl 5-aminopentanoate for methyl 4-aminobutanoate.

m.p. 135°–139° C.; HPLC T$_R$: 3.5 min, 70:30:0.1.

Ester: $^1$H-NMR (CDCl$_3$) δ: 1.8–2.2 (4H,m), 2.55 (2H,t), 3.15 (2H,t), 3.6 (2H,t), 3.65 (3H,s), 3.85 (3H,s), 3.8–4.2 (4H,m), 4.35 (2H,t), 6.7–7.4 (10H,m), 8.05 (1H,dd), 7.8–8.2 (1H,br), 8.8 (1H,d).

Example 8

N-(3-carboxyphenyl)-2-[3-{4-phenoxybutoxy}phenylpropoxy]-5-carboxybenzamide a) N-(3-carbomethoxyphenyl)-2-hydroxy-5-carbomethoxybenzamide

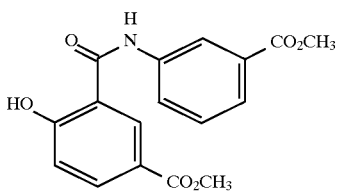

Methyl 4-hydroxyisophthalate (1.0 g) and oxalyl chloride (2.2 ml) were stirred together for 18 h in dry dichloromethane containing one drop of dimethylformamid. Removal of solvent gave a white solid which was dissolved in dichloromethane (30 ml) and added to a solution of methyl 3-aminobenzoate (0.8 g) in dichloromethane (30 ml) and pyridine (6.1 ml) at 0° C. After 18 h this was poured into dilute hydrochloric acid and extracted to give a yellow foam (1.7 g).

$^1$H-NMR (CDCl$_3$) δ: 3.84 (6H,s), 6.8–8.8 (7H,m), 10.7 (2H,br).

b) N-(3-carbomethoxyphenyl)-2-[3-{4-phenoxybutoxy}-phenylpropoxy]-5-carbomethoxybenzamide

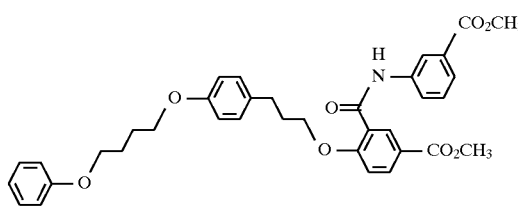

The product of Example 8b was reacted with 1-bromo-3-[4-(4-phenoxybutoxy]phenylpropane following the procedure of Example 5b to give a cream solid which was recrystallised from ethyl acetate-pentane to give a white solid m.p. 110°–111° C.

$^1$H-NMR (CDCl$_3$) δ: 1.9–2.2 (6H,m), 2.68 (2H,m), 3.8 (6H,s), 4.0–4.2 (6H,m), 6.5–7.5 (10H,m), 7.7–8.1 (2H,m), 8.79 (1H,m), 9.7 (1H,br) HPLC T$_R$: 18.3 min, 80:20:0.1.

c) N-(3-carboxyphenyl)-2[-{4-phenoxybutoxy}phenyl-propoxyl-5-carboxybenzamide

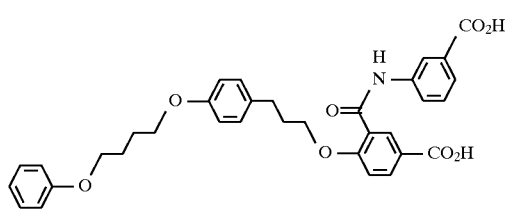

The product of Example 8b was hydrolysed as described in Example 5d to give a white solid m.p. 262°–266° C. HPLC T$_R$: 4.2 min, 80:20:0.1.

Example 9

N-(2-carboxyphenyl)-2-[3-{4-phenoxybutoxy}phenylpropoxy]-5-carboxybenzamide

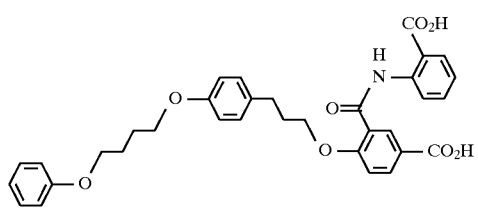

This was prepared following the procedure of Example 8 with the substitution of methyl 2-aminobenzoate for methyl 3-aminobenzoate.

Ester: m.p. 140°–143° C.

$^1$H-NMR (CDCl$_3$+d$^6$-DMSO) δ: 1.9–2.2 (6H,m), 3.77 (3H,s), 3.82 (3H,s), 4.0–4.2 (6H,m), 6.5–7.7 (10H,m), 7.99 (2H,m), 8.7 (2H,m), 11.9 (1H,br)

HPLC T$_R$: 29.6 min, 80:20:0.1.

Acid: m.p. 152°–155° C.

HPLC T$_R$: 3.6 min, 80:20:0.1.

Example 10

N-(4-carboxyphenyl)-2-[3-{4-phenoxybutoxy}phenylpropoxyl]-5-carboxybenzamide

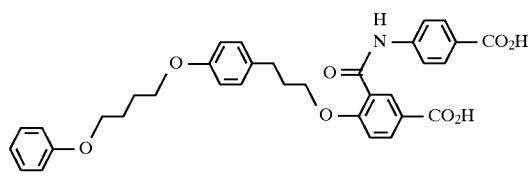

This was prepared following the procedure of Example 8 with the substitution of methyl 4-aminobenzoate for methyl 3-aminobenzoate.

Ester: m.p. 126°–129° C.

$^1$H-NMR (CDCl$_3$) δ: 1.9–2.2 (6H,m), 2.7 (2H,m), 3.84 (6H,s), 4.0–4.2 (6H,m), 6.5–7.4 (10H,m), 7.7 (4H,dd), 7.75 (1H,d), 8.7 (1H,d), 9.78 (1H,s).

HPLC T$_R$: 17.4 min, 80:20:0.1.

Acid: m.p. 218°–221° C.

HPCL T$_R$: 4.4 min, 80:20:0.1.

Example 11

6-aza-6-(5-carboxy-2-[3-{4-phenoxybutoxy}phenylpropoxyl]-5-oxohexanoic acid a) methyl 6-(4-carbomethoxy-2-hydroxyphenyl)-6-aza-5-oxohexanoate

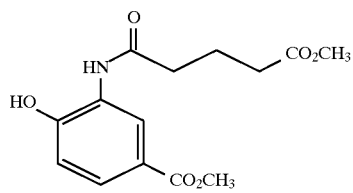

Methyl glutarate (6 g) and diphenyl phosphinic chloride (8.6 ml) were dissolved in ethyl acetate (100 ml) and cooled to –10° C., triethylamine (6.3 ml) was added and stirred for 1 h. A solution of methyl-3-amino-4-hydroxy benzoate (7.5 g) in ethyl acetate (50 ml) containing triethylamine (6.3 ml) was added and the mixture allowed to warm to room temperature.

After 20 h the reaction mixture was filtered and successively washed with dilute hydrochloric acid, aqueous sodium bicarbonate and saturated sodium chloride. This ethyl acetate extract was dried and concentrated in vacuo to give a gum that on trituration with diethyl ether-hexane afforded a solid m.p. 137° C. (5 g).

$^1$H-NMR (CDCl$_3$) δ: 1.9–2.3 (2H,m), 2.3–2.8 (4H,m), 3.65 (3H,s), 3.85(3H,s), 6.95 (1H,d), 7.75 (1H,dd), 8.70 (1H,s).

b) methyl 6-aza-6-(5-carbomethoxy-2-[3-{4-phenoxybutoxy}phenylpropoxy]-5-oxohexanoate

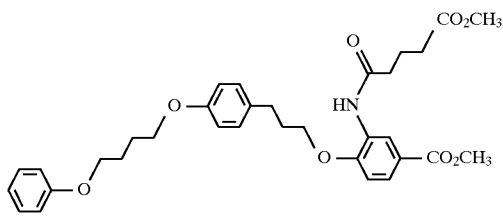

This was prepared using the procedure of Example 5a and the products of Examples 11a and 2a, m.p. 89°–94° C.
$^1$H-NMR (CDCl$_3$) δ: 1.8–2.2 (8H,m), 2.2–2.5 (4H,m), 2.6–2.9 (2H,m), 3.60 (3H,s), 3.80 (3H,s), 3.8–4.2 (6H,m), 6.7–7.4 (1H,m), 7.6–7.9 (2H,m), 8.9 (1H,d).
HPLC T$_R$: 55 min, 60:40:0.1 c) 6-aza-6-(5-carboxy-2-[3-{4-phenoxybutoxy}phenylpropoxy]-5-oxohexanoic acid

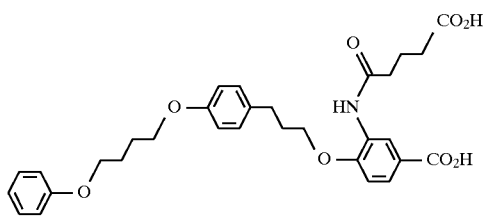

This was prepared from the product of Example 11b following the procedure of Example 4c, m.p. 184°–187° C.
HPCL T$_R$: 8.3 min, 60:40:0.1.

Example 12

7-aza-7-(5-carboxy-2-[3-{4-phenoxybutoxy}phenylpropoxy]-6-oxoheptanoic acid a) Methyl 3-nitro-4-[3-{4-phenoxybutoxy}phenylpropoxyl]-benzoate

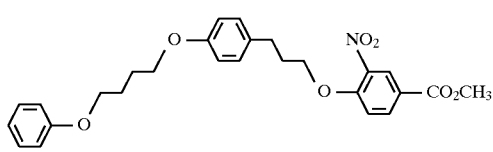

Reaction of methyl 3-nitro-4-hydroxybenzoate and 1-iodo-3-[4-(4-phenoxybutoxy)phenylpropane, following the procedure of Example 3a gave a solid m.p. 110°–113° C.
$^1$H-NMR (CDCl$_3$) δ: 1.6–2.3 (6H,m), 2.75 (2H,t), 3.85 (3H,s), 3.8–4.3 (6H,m), 6.7–7.5 (10H,m), 8.15 (1H,dd), 8.45 (1,d).

b) Methyl 3-amino-4-[3-{4-phenoxybutoxy}phenylpropoxy]-benzoate

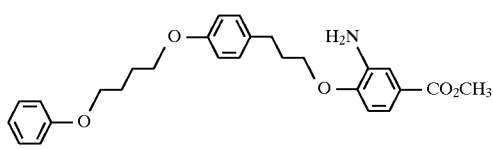

The product of Example 12a (4.1 g) was refluxed with tin(II)chloride (9.7 g) in ethanol (100 ml) until a complete solution was obtained. After cooling this was poured onto ice and extracted with ethyl acetate after neutralisation with sodium hydroxide. The extract was concentrated to give the amine as a tan solid (3.9 g).
$^1$H-NMR (CDCl$_3$) δ: 1.8–2.3 (6H,m), 2.70 (2H,t), 3.5–4.3 (8H,m), 3.80 (3H,s), 6.6–7.5 (12H,m).

c) methyl 7-aza-7-(5-carbomethoxy-2-[3-{4-phenoxybutoxy}phenylpropoxy]-6-oxoheptanoate

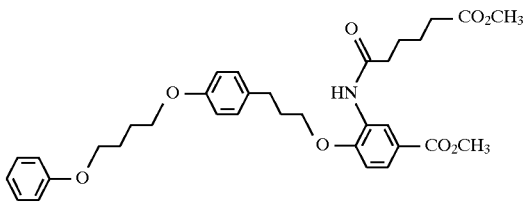

Methyl adipoyl chloride (0.18 g) in dichloromethane (1 ml) was added to a pre-cooled mixture of methyl-3-amino-4-(3-[4-(4-phenoxybutoxy)phenyl]-propoxy) benzoate (0.45 g) and triethylamine (0.15 ml) in dichloromethane (9 ml) at 0° C., then allowed to warm to room temperature. Concentration in vacuo gave a residue that was redissolved in ethyl acetate then washed with dilute hydrochloric acid, aqueous sodium bicarbonate and saturated sodium chloride. This solution was dried and concentrated in vacuo to yield a yellow oil. Column chromatography on silica eluting with 10–50% ethyl acetate-hexane gave the title compound (0.41 g).
$^1$H-NMR (CDCl$_3$) δ: 1.5–2.1 (10H,m), 2.1–2.5 (4H,m), 2.70 (2H,t), 3.60 (3H,s), 3.80 (3H,s), 3.8–4.3 (6H,m), 6.7–7.4 (10H,m), 7.6–7.9 (2H,m), 8.95 (1H,d).

d) 7-aza-7-(5-carboxy-2-[3-{4-phenoxybutoxy}phenylpropoxy]-6-oxoheptanoic acid

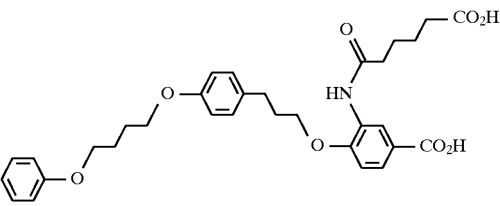

The product of Example 12c was hydrolysed following the procedure of Example 4d to give a white solid m.p. 160°–162° C.
HPLC T$_R$: 3.2 min, 90:10:0.1.

Example 13

5-aza-4-(5-carboxy-2-[3-{4-phenoxybutoxy}phenylpropoxy]-4-oxopentanoic acid

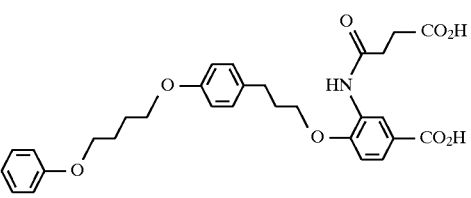

This was prepared following the procedure of Example 12c and 12d substituting methyl succinyl chloride for methyl adipoyl chloride.
m.p. 165°–167° C.; HPLC T$_R$: 2.6 min, 80:20:0.1.

Ester: $^1$H-NMR (CDCl$_3$) δ: 1.8–2.4 (6H,m), 2.85 (2H,t), 3.5 (2H,s), 3.75 (3H,s), 3.85 (3H,s), 3.8–4.3 (6H,m), 6.7–7.4 (10H,m), 7.75 (1H,dd), 9.0 (1H,d), 9.8 (1H,br).

Example 14

4-aza-3-(5-carboxy-2-[3-{4-phenoxybutoxy}phenylpropoxy]-3-oxobutanoic acid

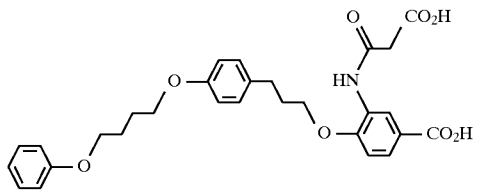

This was prepared following the procedure of Example 12c and 12d substituting methyl malonyl chloride for methyl adipoyl chloride.

m.p. 181°–182° C.; HPLC T$_R$: 3.2 min, 90:10:0.1.

Ester: $^1$H-NMR (CDCl$_3$) δ: 1.8–2.3 (6H,m), (6H,m), 3.65 (3H,s), 3.85 (3H,s), 3.8–4.3 (6H,m), 6.7–7.4 (10H,m), 7.75 (1H,dd), 7.95 (1H,br), 8.95 (1H,d).

Example 15

6-aza-6-(5-carboxy-2-[2-{4-phenoxybutoxy}phenylethoxy]-5-oxohexanoic acid

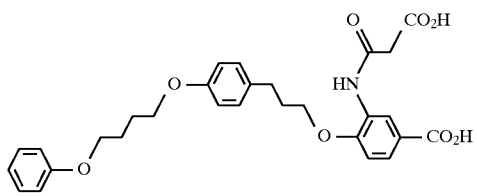

This was prepared following the procedure of Example 12 substituting 1-iodo-2-(4-[4-phenoxybutoxy]phenyl)ethane for 1-iodo-3-(4-[4-phenoxybutoxy]phenyl)-propane.

m.p. 200°–203° C.; HPLC T$_R$: 3.7 min, 70:30:0.1.

Ester: $^1$H-NMR (CDCl$_3$) δ: 1.6–2.1 (6H,m), 2.3 (2H,t), 2.9–3.5 (4H,m), 3.60 (3H,s), 3.85 (3H,s), 3.8–4.3 (4H,m), 4.40 (2H,t), 6.7–7.3 (10H, m), 7.5 (1H,d), 8.05 (1H,dd), 8.80 (1H,d).

m.p. 89°–91° C.; HPLC T$_R$: 6.8 min, 80:20:0.1.

Example 16

5-carboxy-2-[([3-{4-phenoxybutoxy}phenyl]-1-oxopropyl)amino]phenoxyacetic acid a) methyl 5-hydroxy-2-[([3-{4-phenoxybutoxy}phenyl]-1-oxopropyl)amino]-phenoxyacetate

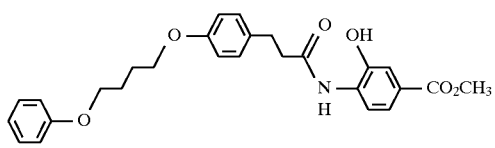

3-(4-[4-phenoxybutoxy]phenyl)propanoic acid (1.0 g) and oxalyl chloride (2.2 ml) were stirred together for 1.5 h in dry dichloromethane containing one drop of dimethylformamide then concentrated to give a white solid.

This was added, in dichloromethane (15 ml) to a solution of methyl 4-amino-3-hydroxybenzoate in dichloromethane (20 ml) and pyridine (4 ml). After stirring for 18 h this was poured into dilute hydrochloric acid and extracted to give a cream solid which was recrystallised from ethyl acetate to give a cream solid (0.9 g) m.p. 159°–160° C.

b) methyl 5-carbomethoxy-2-[([3-{4-phenoxybutoxy}-phenyl]-1-oxopropyl)-amino]phenoxyacetate

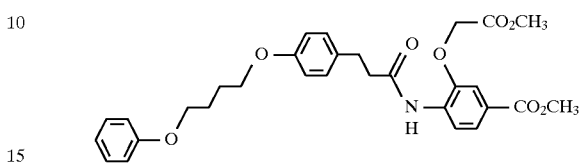

The product of Example 16a (0.3 g), methyl bromoacetate (0.1 g) and potassium carbonate (0.1 g) in dry dimethylformamide (2 ml) were heated overnight at 60° C. The solution was poured into water and extracted with ethyl acetate to give a yellow solid, recrystallisation from ethyl acetate gave a cream solid (0.25 g). m.p. 133°–134° C.

$^1$H-NMR (CDCl$_3$) δ: 1.9–2.1 (4H,m) 3.74 (3H,s), 3.84 (3H,s), 4.0–4.2 (4H,m), 6.7–7.1 (5H,m), 7.1–7.4 (4H,m), 7.46 (1H,s), 7.7 (1H,m), 8.5 (1H,s).

HPLC T$_R$ 7.1 min 80:20:0.1 c) 5-carboxy-2-[([3-{4-phenoxybutoxy}phenyl]-1-oxopropyl)amino]phenoxyacetic acid

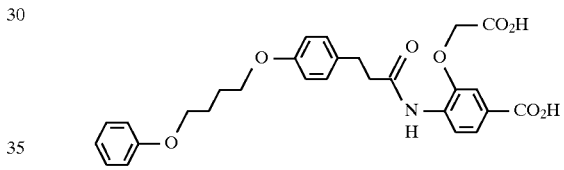

The product of Example 16b was hydrolysed as described in Example 5d to give a white solid m.p. >250° C.

HPLC T$_R$ 2.3 min 80:20:0.1.

Example 17

5-carboxy-2-[([3-{4-phenoxybutoxy}phenyl-1-oxopropyl)amino]phenoxybutanoic acid

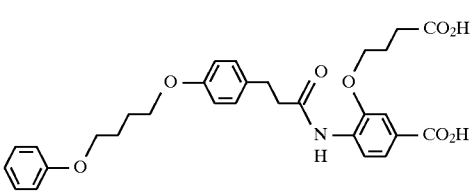

This was prepared following the procedure of Example 16 substituting methyl 4-bromobutanoate for methyl 2-bromoacetate.

ester: m.p. 108° C.

$^1$H-NMR (CDCl$_3$) δ: 1.9–2.1 (4H,m), 2.1–2.5 (4H,m), 2.6–3.0 (4H,m), 3.57 (3H,s), 3.80 (3H,s), 4.0–4.2 (6H,m), 6.6–7.0 (5H,m), 7.0–7.3 (4H,m), 7.48 (1H,s), 7.7 (1H,m), 8.0 (1H,s), 8.5 (1H,s).

HPLC T$_R$ 9.2 min 80:20:0.1 acid: m.p. 177°–179° C.

HPLC T$_R$ 3.7 min 80:20:0.1

Example 18

5-carboxy-2-[([3-{4-phenoxybutoxy}phenyl]-1-oxopropyl)amino]phenoxyhexanoic acid

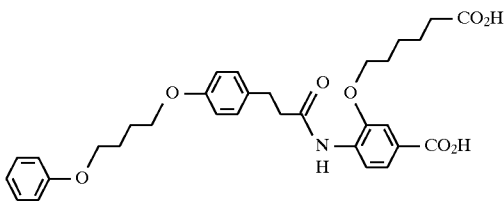

This was prepared following the procedure of Example 16 substituting methyl 6-bromohexanoate for methyl 2-bromoacetate.

ester: $^1$H-NMR (CDCl$_3$) δ: 1.5 (6H,m), 1.9–2.1 (4H,m), 2.2 (2H,m), 2.7 (4H,m), 3.52 (3H,s), 3.78 (3H,s), 4.0–4.2 (6H,m), 6.5–6.9 (5H,m), 7.0–7.2 (4H,m), 7.39 (1H,s), 7.5 (1H,m), 8.2 (1H,m), 8.8 (1H,s).

HPLC $T_R$ 11.9 min 80:20:0.1 acid: m.p. 161°–164° C.

HPLC $T_R$ 4.1 min 80:20:0.1

Example 19

5-carboxy-2-[([3-{4-phenoxybutoxy}phenyl]-1-oxopropyl)amino]phenylacetic acid a) methyl 4-nitro-3-trifluoromethylsulfonyloxybenzoate

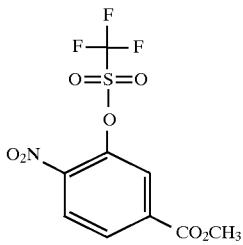

Methyl 3-hydroxy-4-nitrobenzoate (26.5 g) was dissolved in dry dichloromethane (120 ml) and triethylamine (42 ml) was added. This solution was cooled to −20° C. and trifluoromethanesulfonic anhydride (25.3 ml) was added dropwise at <−10° C. The mixture was allowed to warm to room temperature. After 1 hour it was concentrated in vacuo, redissolved in diethyl ether and washed with dilute hydrochloric acid, aqueous sodium bicarbonate and saturated sodium chloride. This was dried and concentrated in vacuo. Crystallisation from diethyl ether-heptane (1:3) gave pale yellow needles. m.p. 91.5°–92.5° C., 40.8 g.

$^1$H-NMR (CDCl$_3$) δ: 4.00 (3H,s), 8.0–89.3 (3H,m).

b) di-t-butyl (5-carbomethoxy-2-nitrophenyl)malonate

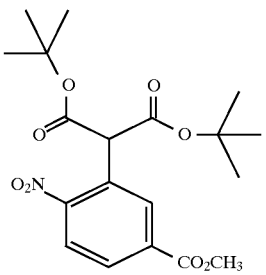

Methyl 4-nitro-3-trifluoromethanesulfonyloxybenzoate (39.5 g), di-t-butylmalonate (29.6 ml) and potassium carbonate (83 g) were refluxed in acetonitrile (250 ml) for 20 hours. The cooled mixture was diluted with ethyl acetate and poured into a aqueous ammonium chloride. Ethyl acetate extracts were washed with aqueous sodium carbonate (5%), aqueous ammonium chloride and saturated sodium chloride then dried and concentrated in vacuo. Crystallisation of the crude product was achieved on standing at −20° C. These crystals were triturated with diethyl ether-pentane and filtered to give the product m.p. 93°–94° C., 8.8 g.

$^1$H-NMR (CDCl$_3$) δ: 1.50 (18H,s), 3.90 (3H,s), 5.00 (1H,s), 8.0–8.3 (3H,m).

c) t-butyl (5-carbomethoxy-2-nitro)phenylacetate

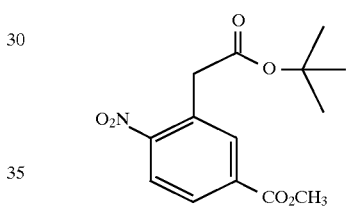

Methyl 3-di-tert-butylmalonyl-4-nitro benzoate (8.7 g) was dissolved in dimethylsulfoxide (50 ml) containing water (0.8 ml) and heated at 150° C. for 1 hour. The cooled mixture was extracted into diethyl ether and washed with aqueous sodium bicarbonate and saturated sodium chloride then dried and concentrated in vacuo. This crude product was purified by column chromatography on silica in 20% ethyl acetate-pentane to afford a pale yellow solid m.p. 79°–81° C., 3.2 g.

$^1$H-NMR (CDCl$_3$) δ: 1.45 (9H,s), 3.95 (3H,s), 4.00 (2H, s), 7.9–8.1 (3H,m).

d) t-butyl (2-amino-5-carbomethoxy)phenylacetate

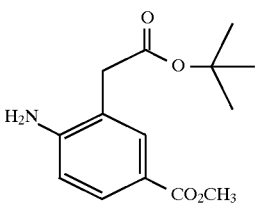

tert-Butyl-5-carbomethoxy-2-nitro phenyl acetate (3.2 g) was dissolved in ethyl acetate (50 ml) and 10% palladium on charcoal (0.5 g) added. This mixture was stirred under an atmosphere of hydrogen for 1 hour until uptake had ceased. It was filtered through Celite, dried and concentrated in vacuo to afford a white solid m.p. 85°–87° C., 2.8 g.

$^1$H-NMR (CDCl$_3$) δ: 1.45 (9H,s), 3.45 (2H,s), 3.85 (3H, s), 4.65 (2H,br), 6.65 (1H,d), 7.6–7.9 (2H,m).

e) t-butyl 5-carbomethoxy-2-[([3-{4-phenoxybutoxy}-phenyl]-1-oxopropyl)-amino]phenylacetate

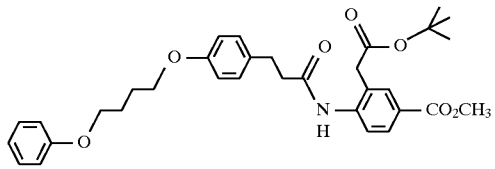

3-(4-[4-Phenoxybutoxy]phenyl) propionic acid (1.4 g) was suspended in dry dichloromethane (20 ml). This solution was added to a pre-cooled mixture of tert-butyl-2-amino-5-carbomethoxy phenyl acetate (41 g) and pyridine (1.6 ml) in dry dichloromethane (20 ml) at 0°–5° C. It was stirred at room temperature for 2 hours, then poured into water and extracted with dichloromethane. These extracts were washed with aqueous sodium bicarbonate and saturated sodium chloride, then dried and concentrated in vacuo to give a white solid. Crystallisation from diethyl ether-heptane (12:1) gave white solid m.p. 92°–93° C., 1.8 g.

$^1$H-NMR (CDCl$_3$) δ: 1.40 (9H,s), 1.8–2.1 (4H,m), 2.6–3.1 (4H,m), 3.30 (2H,s), 3.85 (3H,s), 3.8–4.2 (4H,m), 6.7–7.3 (10H,m), 7.8–8.1 (2H,m), 9.1 (1H,br).

f) 5-carboxy-2-[([3-{4-phenoxybutoxy}phenyl]-1-oxopropyl)amino]phenylacetic acid

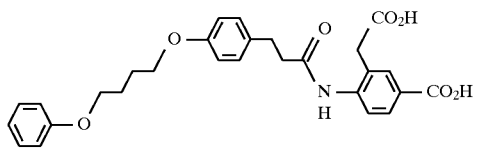

The product of Example 19e was hydrolysed as described in Example 4c to afford a white solid m.p. 222°–225° C.
HPLC T$_R$: 2.3 min, 80:20:0.1.

Example 20

5-carboxy-2-[([3-{4-phenoxybutoxy}phenyl]-1-oxopropyl)amino]phenyl-5-thiapentanoic acid a) Methyl 4-thioacetylbutanoate

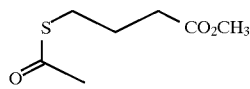

Methyl 4-chlorobutanoate (6.2 g), potassium thioacetate (10.3 g) and sodium iodide (0.5 g) were refluxed in acetone (50 ml) for 22 hours. Concentration in vacuo gave a residue that was redissolved in ethyl acetate-water. These ethyl acetate extracts were washed with aqueous sodium metabisulfite, water and saturated sodium chloride, then dried and concentrated in vacuo to afford a black liquid (7.4 g).

$^1$H-NMR (CDCl$_3$) δ: 1.7–2.2 (2H,m), 2.2–2.6 (2H,m), 2.30 (3H,s), 2.90 (2H,t), 3.65 (3H,s).

b) 4-mercaptobutanoic acid

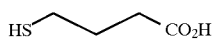

Methyl 4-thioacetylbutanoate (5.0 g) was dissolved in tetrahydrofuran (100 ml) to which was added a solution of sodium hydroxide (3.5 g) in water (60 ml), the mixture was stirred for 3.5 hours, then concentrated in vacuo and diluted with aqueous ammonium chloride and washed with ethyl acetate. The aqueous phase was acidified with dilute hydrochloric acid and extracted with ethyl acetate. These extracts were washed with water and saturated sodium chloride, then dried and concentrated in vacuo to afford a dark solid residue (3.2 g). $^1$H-NMR showed this to be a 1:1 mixture of disulphide to thiol.

$^1$H-NMR (CDCl$_3$+d$^6$-DMSO) δ: 1.35 (1H,t), 1.7–2.3 (2H,m), 2.40 (2H,m), 2.70 (2H,t), 9.0 (1H,br).

c) 5-(4-carboxy-2-nitrophenyl)-5-thiapentanoic acid

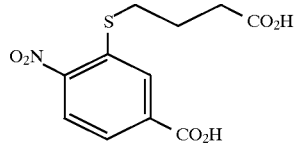

4-Chloro-3-nitrobenzoic acid (0.31 g) was dissolved in tetrahydrofuran (2 ml) and warmed to 60° C. with aqueous sodium hydroxide (0.10 g). 4-Mercaptobutanoic acid (0.40 g) in tetrahydrofuran (4 ml) was treated for 15 minutes with tributyl phosphine (0.80 ml), then with aqueous sodium hydroxide (0.20 g). After 20 minutes this mixture was added to the sodium benzoate and for 2 hours at 60° C. It was diluted with water and extracted with ethyl acetate. The aqueous phase was acidified and extracted with ethyl acetate. These extracts were washed with water and saturated sodium chloride, then dried and concentrated in vacuo to afford a yellow solid (0.33 g).

d) methyl 5-(4-carbomethoxy-2-nitrophenyl)-5-thiapentanoate

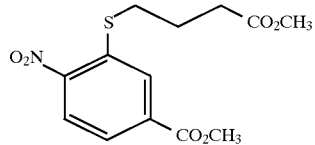

The product of Example 21c (0.67 g) was refluxed in methanolic hydrogen chloride for 2 hours. After cooling it was concentrated in vacuo and redissolved in ethyl acetate. This solution was washed with aqueous sodium bicarbonate, water and saturated sodium chloride, then dried and concentrated in vacuo to afford a solid residue (0.64 g). Column chromatography on silica in 40% ethyl acetate-pentane yielded a pale yellow crystalline solid (0.45 g) m.p. 112°–114° C.

$^1$H-NMR (CDCl$_3$) δ: 1.8–2.2 (2H,m), 2.45 (2H,t), 3.10 (2H,t), 3.70 (3H,s), 3.95 (3H,s), 7.50 (1H,d), 8.15 (1H,dd), 8.80 (1H,d).

e) methyl 5-(2-amino-4-carbomethoxy phenyl)-5-thiapentanoate

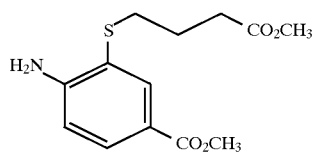

The product of Example 21d (0.11 g), tin(II) chloride (0.41 g) and ethyl acetate (10 ml) were heated to 60° C. for 2 hours. The mixture was poured into ethyl acetate and washed with aqueous sodium bicarbonate, water and saturated sodium chloride, then dried and concentrated in vacuo to yield a yellow residue (0.10 g).

¹H-NMR (CDCl₃) δ: 1.85 (2H,m), 2.40 (2H,t), 2.80 (2H,t), 3.60 (3H,s), 3.80 (3H,s), 4.30 (2H,m), 7.30 (3H,m).

f) methyl 5-carbomethoxy-2-[([3-{4-phenoxybutoxy}-phenyl]-1-oxopropyl)amino]phenyl-5-thiapentanoate

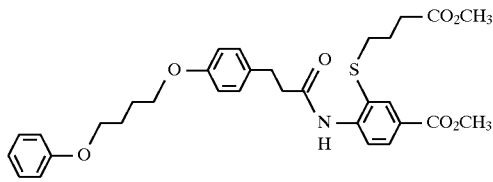

The product of Example 3c (0.14 g) was suspended in dichloromethane (4 ml) and oxalyl chloride (0.30 ml) plus a drop of dimethylformamide was added. After 30 minutes this solution was concentrated in vacuo to give a solid acid chloride. This was redissolved in dichloromethane (4 ml) and added to a cooled solution of the product of Example 21e (0.10 g) in dichloromethane (4 ml) and pyridine (0.30 ml) at 0° C. After 2 hours the mixture was allowed to warm to room temperature and poured into dilute hydrochloric acid. Ethyl acetate extracts were washed with aqueous sodium bicarbonate, water and saturated sodium chloride, then dried and concentrated in vacuo to give a yellow residue (0.09 g). Purification by preparative TLC and then RP-HPLC (Zorbax) in acetonitrile-water (70:30) gave a white solid m.p. 92°–94° C., 0.05 g.

¹H-NMR (CDCl₃) δ: 1.7–2.2 (6H,m), 2.40 (2H,t), 2.6–3.2 (6H,m), 3.60 (3H,s), 3.85 (3H,s), 3.8–4.2 (4H,m), 6.6–7.8 (11H,m), 8.05 (1H,s), 8.80 (1H,s).

HPLC T$_R$: 12.50 min, 70:30:01.

g) 5-carboxy-2-[([3-{4-phenoxybutoxy}phenyl]-1-oxopropyl)amino]phenyl-5-thiapentanoic acid

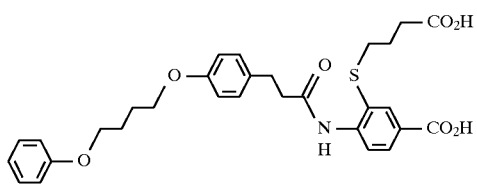

The product of Example 20f (0.05 g) was hydrolysed as described in Example 4c to afford a white solid m.p. 201°–203° C., 0.05 g.

HPLC T$_R$: 3.40 min, 70:30:01.

Example 21

5-carboxy-2-[([3-{4-phenoxybutoxy}phenyl]-1-oxopropyl)amino]phenyl-5-oxopentanoic acid a) 6-carboxy-2-[(4-carboxyphenyl)hydrazino]-hexanoic acid

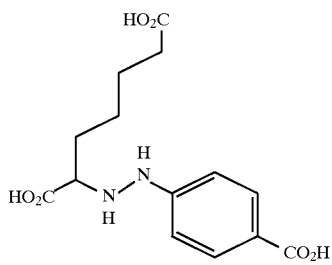

Ethyl 6-carboxy-2-[(4-carbethoxyphenyl)hydrazino]-hexanonate was prepared from 4-aminobenzoic acid (27 g) and ethyl 2-cyclohexanone carboxylate as described by Witte and Boekelheide (J.Org.Chem. (1972) 37, 2849). The resultant orange solid (34 g) was refluxed for 30 min in boron trifluoride etherate (100 ml) and ethanol (200 ml). Aqueous work-up, extraction with dichloromethane and chromatography on alumina with 2% methanol in dichloromethane gave the acid as a yellow solid (28 g).

b) methyl 4-(2,5-dicarbomethoxyindol-3-yl)butanoate

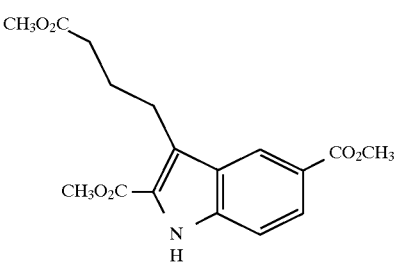

The product of Example 21a (28 g) was refluxed for 168 h in boron trifluoride etherate (100 ml) and methanol (200 ml). Aqueous work-up and extraction with dichloromethane gave an off-white solid (16 g) m.p. 136°–138° C.

¹H-NMR (CDCl₃) δ: 2.1 (2H,t), 2.4 (2H,t), 3.2 (2H,t), 3.65 (3H,s), 7.4 (1H,d), 8.1 (1H,d), 8.5 (1H,s), 9.5 (2H,br).

c) methyl 5-([2-(carbomethoxyacetyl)amino-5-carbomethoxy]-phenyl)5-oxopentanoate

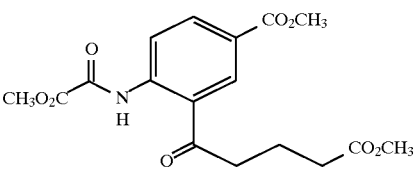

Chromium (VI) oxide (9 g) in aqueous acetic acid was added to a suspension of the product of Example 21b (10 g) in acetic acid (50 ml) and stirred overnight. Aqueous work-up, extraction with dichloromethane and recrystallisation from aqueous methanol to gave a yellow solid (8.0 g) m.p. 120°–121° C.

¹H-NMR (CDCl₃) δ: 2.1 (2H,t), 2.3 (2H,t), 3.1 (2H,t), 3.58 (3H,s), 3.81 (3H,s), 3.89 (3H,s), 8.1 (1H,d), 8.6 (1H,d), 8.8 (1H,s), 12.1 (1H,br).

d) methyl 5-([2-amino-5-carbomethoxy]-phenyl)-5-oxopentanoate

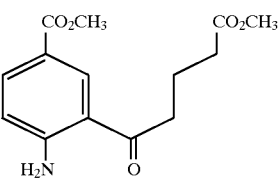

The product of Example 21c (7.3 g) was refluxed in concentrated sulfuric acid (5 ml) and methanol (100 ml) for 3 h then poured onto ice and extracted with dichloromethane to give a white solid which was recrystallised from aqueous methanol to give pale yellow plates (4.7 g) m.p. 133°–134° C.

¹H-NMR (CDCl₃) δ: 2.1 (2H,t), 2.3 (2H,t), 3.05 (2H,t), 3.68 (3H,s), 3.85 (3H,s), 6.7 (1H,d), 6.9 (2H,br), 7.9 (1H, dd), 8.4 (1H,d).

e) methyl 5-carbomethoxy-2-[([3-{4-phenoxybutoxy}-phenyl]-1-oxopropyl)amino]phenyl-5-oxopentanoate This was prepared following the procedure of Example 16b, substituting the product of Example 21d (1.1 g) for that of Example 16a, as white needles (1.8 g) m.p. 99°–100° C.

$^1$H-NMR (CDCl$_3$) δ: 1.8–2.1 (6H,m), 2.1–2.3 (4H,m), 2.8 (2H,t), 3.0 (2H,t), 3.62 (3H,s), 3.88 (3H,s), 4.0–4.2 (4H,m), 6.7–7.4 (9H,m), 8.1 (1H,dd), 8.6 (1H,d), 8.9 (1H,d), 11.8 (1H,s).

HPLC T$_R$: 10.1 min, 80:20:0.1 f) 5-carboxy-2-[([3-{4-phenoxybutoxy}phenyl]-1-oxopropyl)amino]phenyl-5-oxopentanoic acid The product of Example 21e was hydrolysed following the procedure of Example 5d to give a white solid m.p. 170°–173° C.

$^1$H-NMR (CDCl$_3$) δ: 2.0–2.2 (8H,m), 2.5–3.3 (6H,m), 4.0–4.2 (4H,m), 6.8–7.5 (10H,m), 8.3 (1H,d), 9.1 (1H,s), 11.8 (2H,br), 12.1 (1H,s).

HPLC T$_R$: 3.3 min, 80:20:0.1.

Examples 22–28

The following Examples were prepared following the procedure of Example 16 using dimethyl 4-amino-isophthalate or dimethyl 5-amino-isophthalate plus the indicated acid.

From 3-(4-[4-phenoxybutoxy]phenyl)propanoic acid:

Example 22

3-carboxy-4-([3-{4-phenoxybutoxy}phenyl]-1-oxopropyl)aminobenzoic acid

Example 23

3-carboxy-5-([3-{4-phenoxybutoxy}phenyl]-1-oxopropyl)aminobenzoic acid m.p. 264°–266° C.; HPLC T$_R$: 2.6 min, 80:20:0.1.

Ester: $^1$H-NMR (CDCl$_3$) δ: 1.8–2.1 (4H,m), 2.5–3.2 (4H,m), 3.85 (6H,s), 3.8–4.2 (4H,m), 6.7–7.5 (9H,m), 8.05 (1H,s), 8.35 (3H,s).

From 4-(4-[4-phenoxybutoxy]phenyl)butanoic acid:

Example 24

3-carboxy-4-([4-{4-phenoxybutoxy}phenyl]-1-oxobutyl)aminobenzoic acid m.p. 193°–195° C.; HPLC T$_R$: 2.6 min, 70:30:01.

Ester: $^1$H-NMR (CDCl$_3$) δ: 1.8–2.2 (6H,m), 2.3–2.8 (4H,m), 3.85 (6H,s), 3.8–4.1 (4H,m), 6.6–7.4 (9H,m), 8.15 (1H,dd), 8.8 (1H,d), 8.7–9.2 (1H,br), 11.5 (1H,br).

Example 25

3-carboxy-5-([4-{4-phenoxybutoxy}phenyl]-1-oxobutyl)aminobenzoic acid m.p. 228°–232° C; HPLC T$_R$: 2.9 min, 70:30:0.1.

Ester: $^1$H-NMR (CDCl$_3$) δ: 1.8–2.1 (6H,m), 2.2–2.8 (4H,m), 3.85 (6H,s), 3.8–4.1 (4H,m), 6.7–7.4 (9H,m), 8.05 (1H,s), 8.35 (3H,s).

From 4-(4-[4-phenoxybutoxy]phenyl)ethanoic acid:

Example 26

3-carboxy-4-([2-{4-phenoxybutoxy}phenyl]-1-oxoethyl)aminobenzoic acid

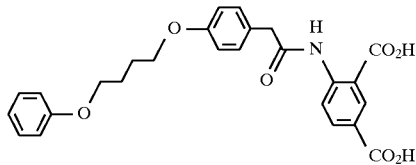

m.p. 180°–184° C.; HPLC $T_R$: 4.9 min, 70:30:0.1.
Ester: m.p. 103°–106° C., $^1$H-NMR (CDCl$_3$) δ:
HPLC $T_R$: 9.7 min, 70:30:0,1.

Example 27

3-carboxy-5-([2-{4-phenoxybutoxy}phenyl]-1-oxoethyl)aminobenzoic acid

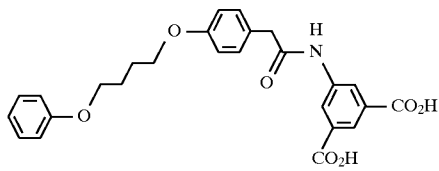

HPLC $T_R$: 2.8 min, 60:40:0.1
Ester: m.p. 140° C., $^1$H-NMR (CDCl$_3$) δ:
HPLC $T_R$: 7.4 min, 75:25:0.1.
From 4-[4-phenoxybutoxy]phenoxyacetic acid:

Example 28

3-carboxy-4-([2-{4-phenoxybutoxy}phenoxy]-1-oxoethyl)aminobenzoic acid

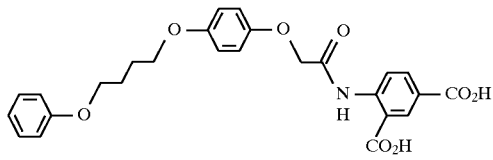

m.p. 222°–226° C.; HPLC $T_R$: 2.7 min, 60:40:0.1.
Ester: m.p. 125°–130° C., $^1$H-NMR (CDCl$_3$) δ:
HPLC $T_R$: 10.4 min, 80:20:0.1.

Example 29

2-(3-[4-{4-phenoxybutoxy}phenyl]propoxy)-5-(methylsulfonylamino)benzoic acid a) methyl 2-(3-[4-{4-phenoxybutoxy}phenyl]propoxy)-5-nitrobenzoate

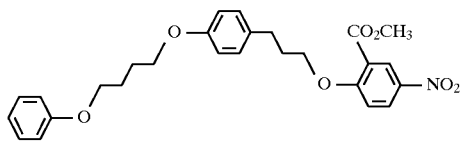

This was prepared from methyl 2-hydroxy-5-nitrobenzoate (2.7 g) and 1-bromo-3-[4-(4-phenoxybutoxy) phenyl]propane (1.6 g), following the procedure of Example 4b, as a yellow solid (1.6 g) m.p. 91°–93° C.

$^1$H-NMR (CDCl$_3$) δ: 1.9–2.2 (6H,m), 2.82 (2H,t), 3.92 (3H,t), 3.9–4.2 (6H,m), 6.6–7.4 (10H,m), 8.30 (1H,dd), 8.71 (1H,dd).

b) methyl 2-(3-[4-{4-phenoxybutoxy}phenyl]propoxy)-5-aminobenzoate

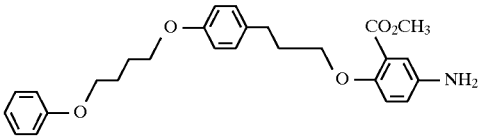

The product of Example 29a (1.7 g) was refluxed with tin(II)chloride (3.9 g) in ethanol (50 ml) until a complete solution was obtained. After cooling this was poured onto ice and extracted with ethyl acetate after neutralisation with sodium hydroxide. The extract was concentrated to give the amine as a yellow oil (1.4 g).

$^1$H-NMR (CDCl$_3$) δ: 1.9–2.1 (6H,m), 2.6 (2H,q), 3.6 (2H,m), 3.87 (3H,s), 3.8–4.1 (6H,m), 6.6–7.5 (12H,m).

c) methyl 2-(3-[4-{4-phenoxybutoxy}phenyl]propoxy)-5-(methylsulfonylamino)benzoate

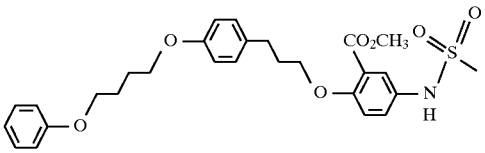

The product of Example 29b (0.4 g) was dissolved in dichloromethane (10 ml) and triethylamine (0.1 ml), then stirred for 3 h with methanesulfonyl chloride (0.06 ml). The solution was poured into water and extracted with ether to give a yellow oil which on trituration with ether gave the title compound as a white solid (0.14 g) m.p. 86°–88° C.

$^1$H-NMR (CDCl$_3$) δ: 1.8–2.2 (6H,m), 2.4–2.7 (2H,m), 3.25 (3H,s), 3.6 (2H,m), 3.75 (3H,s), 3.9–4.1 (6H,m), 6.7–7.3 (12H,m), 7.8 (1H,d).

HPLC $T_R$: 6.9 min, 80:20:0.1.

d) 2-(3-[4-{4-phenoxybutoxy}phenyl]propoxy)-5-(methylsulfonylamino)benzoic acid

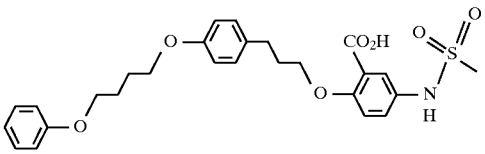

The product of the above Example was treated with lithium hydroxide in aqueous tetrahydrofuran for 18 h. After acidification it was extracted with ethyl acetate to give the acid as a white solid (0.11 g) m.p. 110°–112° C.

HPLC $T_R$: 4.1 min, 80:20:0.1.

Example 30

2-(3-[4-{4-phenoxybutoxy}phenyl]propoxy)-5-(phenylsulfonylamino)benzoic acid

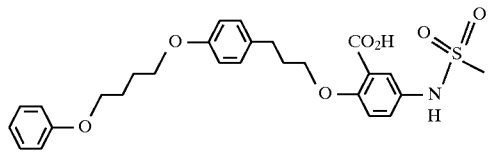

This was prepared from the product of Example 29b and phenylsulfonyl chloride following the procedures of Examples 29c and 29d as a brown solid m.p. 77°–79° C. Ester: $^1$H-NMR (CDCl$_3$)δ: 1.8–2.2 (6H,m), 2.5–3.0 (2H,m), 3.8 (3H,s), 3.8–4.1 (6H,m), 6.7–8.0 (18H,m).

HPLC T$_R$: ester 15.9 min; acid 7.9 min 80:20:01.

Example 31

4-aza-5-(5-[methylsulfonylamino]-2-(3-[4-{4-phenoxybutoxy}phenyl]propoxy)phenyl)-5-oxopentanoic acid a) methyl 4-aza-5-([2-hydroxy-5-nitro)phenyl)-5-oxopentanoate

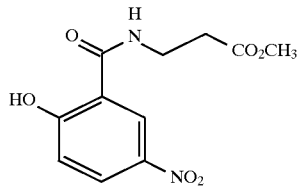

Methyl 3-aminopropanoate hydrochloride (2.8 g), 2-hydroxy-5-nitrobenzoic acid, dimethylaminopropylethylcarbodiimide (3.7 g) and triethylamine (2.8 ml) were stirred together in dry dichloromethane (50 ml) for 20 h. The solution was poured into water and extracted with dichloromethane to give a solid which was recrystallised from ethanol to give white needles (1.3 g) m.p. 155°–156° C.

$^1$H-NMR (d$^6$-DMSO) δ: 2.66 (2H,t), 3.53 (2H,m), 3.64 (3H,s), 7.03 (1H,d), 8.23 (1H,dd), 8.85 (1H,d), 9.2 (1H,br).

b) methyl 4-aza-5-([2-(3-[4-{4-phenoxybutoxy}phenyl]propoxy)-5-nitro)phenyl)-5-oxopentanoate

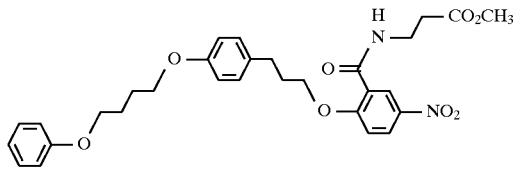

This was prepared from the products of Example 31a (1.2 g) and Example 1c (1.6 g) following the procedure of Example 4a to give a yellow oil which was crystallised from ethyl acetate-hexane as yellow needles (0.4 g) m.p. 90°–91° C.

$^1$H-NMR (CDCl$_3$) δ: 1.8–2.1 (4H,m), 2.2–2.5 (2H,m), 2.5–4.9 (4H,m), 3.55 (3H,s), 3.6–4.2 (8H,m), 6.6–7.3 (10H,m), 8.0–8.2 (2H,m), 8.85 (1H,d).

c) methyl 4-aza-5-([5-amino-2-(3-[4-{4-phenoxybutoxy}-phenyl)propoxy)phenyl)-5-oxopentanoate

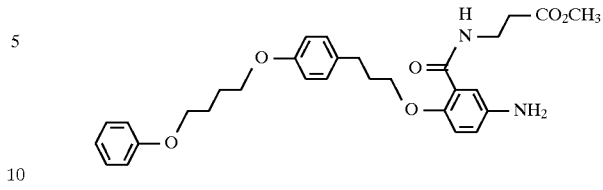

Reduction of the product of Example 31b with tin(II) chloride, following the procedure of Example 29b, gave the amine as a red oil.

$^1$H-NMR (CDCl$_3$) δ: 1.8–2.1 (6H,m), 2.3–2.6 (4H,m), 3.65 (3H,s), 3.8–4.2 (6H,m), 6.6–7.4 (12H,m), 8.4 (1H,br).

d) methyl 4-aza-5-([5-(methanesulfonyl)amino-2-(3-[4-{4-phenoxybutoxy}-phenyl]propoxy)-phenyl)-5-oxopentanoate

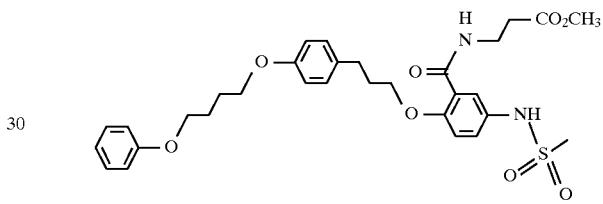

Reaction of the product of Example 31c with methanesulfonyl chloride, following the procedure of Example 29c, gave the sulfonamide as an orange solid m.p. 135°–136° C.

$^1$H-NMR (CDCl$_3$) δ: 1.8–2.1 (6H,m), 2.25 (2H,m), 2.7 (4H,m), 2.88 (3H,s), 3.60 (3H,s), 3.8–4.1 (6H,m), 6.7–7.2 (10H,m), 7.75 (1H,dd), 8.38 (1H,d), 8.8 (2H,br).

HPLC T$_R$: 5.2 min, 80:20:0.1.

e) 4-aza-5-(5-[methylsulfonylamino]-2-(3-[4-{4-phenoxybutoxy}phenyl]-propoxy)phenyl)-5-oxopentanoic acid

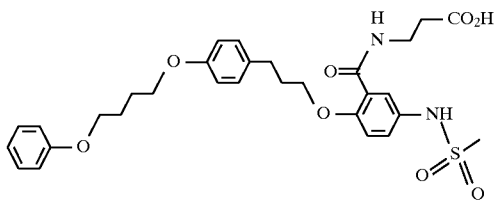

The product of Example 31d was hydrolysed as described in Example 4c to 5 give a fawn solid m.p. 153°–154° C.

HPLC T$_R$: 3.7 min, 80:20:0.1.

Example 32

5-aza-5-(5-carboxy-2-(3-[4-{4-phenoxybutoxy}phenyl]-1-thiapropyl)phenyl)-4-oxopentanoic acid a) 3-nitro-4-(3-[4-{4-phenoxybutoxy}phenyl]-1-thiapropyl)benzoic acid

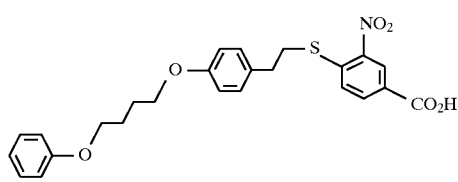

The product of Example 2 (10.6 g), 4-chloro-3-nitrobenzoic acid (19 g) and sodium hydroxide (6 g) in 25% aqueous ethanol (650 ml) were refluxed together for 1 h. The mixture was cooled and filtered. The yellow solid collected was dried and recrystallised from ethanol to give the thioether as a pale yellow powder (9.3 g) m.p. 134°–136° C.

b) 3-amino-4-(3-[4-{4-phenoxybutoxy}phenyl]-1-thiapropyl)benzoic acid

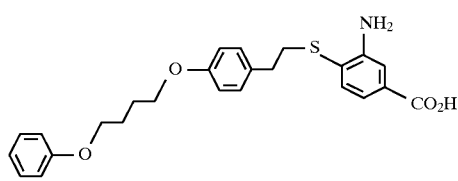

The product of Example 32a (7.2 g) was refluxed with tin(II)chloride (17.7 g) in ethanol (200 ml) for 4 h. The solution was cooled, poured into water and extracted with ethyl acetate. Removal of the solvent gave a quantitative yield of the amine as a yellow powder m.p. 114°–116° C.

c) methyl 5-aza-5-(5-carboxy-2-(3-[4-{4-phenoxybutoxy}-phenyl]-1-thiapropyl)phenyl-4-oxopentanoate

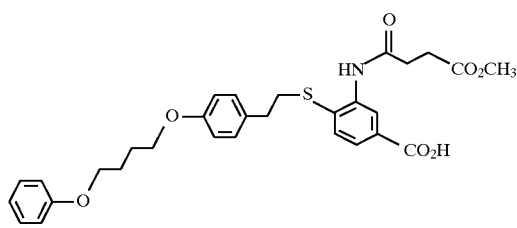

The product of Example 32b (6.4 g), triethylamine (5.3 ml) and methyl 3-chloroformylpropionate were stirred together overnight in dichloromethane (100 ml). The resulting mixture was poured into water and the organic phase separated and concentrated to give a sticky yellow solid. Trituration with ether gave the title acid as a cream solid (1.6 g) 138°–140° C.

$^1$H-NMR (d$^6$-DMSO+CDCl$_3$) δ: 1.8–2.1 (4H,m), 2.5–3.3 (8H,m), 3.59 (3H,s), 3.8–4.1 (4H,m), 6.8–7.3 (10H,m), 7.45 (1H,d), 7.75 (1H,d), 8.05 (1H,d), 9.4 (1H,br).

HPLC T$_R$: 3.5 min, 90:10:0,1.

d) 5-aza-5-(5-carboxy-2-(3-[4-{4-phenoxybutoxy}phenyl]-1-thiapropyl) -phenyl)-4-oxopentanoic acid

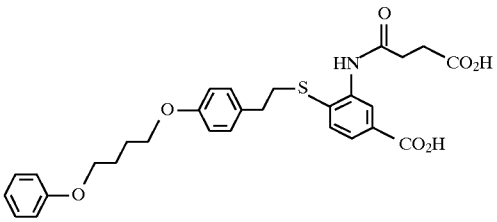

The product of Example 32c was stirred for 72 h with lithium hydroxide in tetrahydrofuran, then acidified and extracted with ethyl acetate. The resultant solid was washed with ether to give a white solid m.p. 176°–178° C.

HPLC T$_R$: 3.7 min, 80:20:0.1.

Example 33

6-aza-6-(5-carboxy-2-(3-4-{4-phenoxybutoxy}phenyl]-1-thiapropyl)phenyl)-5-oxohexanoic acid

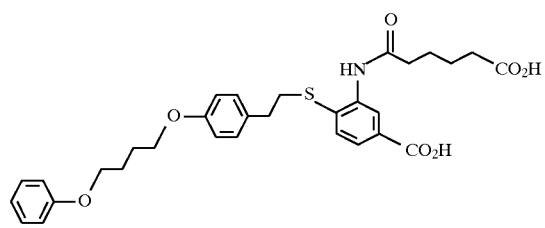

This was prepared from the product of Example 32b following the procedure of Examples 32c and 32d, substituting methyl 4-chloroformalybutanoate for methyl 3-chloroformylpropanoate, to give a white solid m.p. 110°–112° C.

$^1$H-NMR (CDCl$_3$)ester δ: 1.7–2.1 (8H,m), 2.1–2.4 (4H,m), 2.5–3.0 (4H,m), 3.64 (3H,s), 3.8–4.1 (4H,m), 6.8–7.2 (10H,m), 7.3–8.0 (2H,m), 8.8–9.1 (2H,br).

HPLC T$_R$: 3.2 min, 80:20:0.1.

Example 34

5-aza-5-(5-methylsulfonylamino]-2-(3-[4-{4-phenoxybutoxy}phenyl]-1-thiapropyl)phenyl-4-oxopentanoic acid

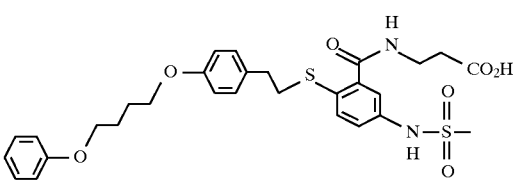

This was prepared from the product of Example 32b following the procedures of Example 29c and Example 4.

ester: HPLC T$_R$: 7.5 min, 70:30:0.1.

$^1$H-NMR (CDCl$_3$) δ: 1.8–2.0 (6H,m), 2.5 (6H,m), 2.9 (3H,s), 3.6 (3H,s), 4.0–4.2 (4H,m), 6.7–7.4 (10H,m), 7.8 (1H,s), 7.95 (1H,tr), 8.6 (1H,br).

HPLC T$_R$: 4.6 min, 70:30:01.

Example 35

3-([4-carboxy-1-oxobutyl)amino-4-(3-[4-{4-phenoxybutoxy}phenyl]-1-thiapropyl)phenyl)-N-phenylsulfonylbenzamide a) 3-([4-carbomethoxy-1-oxobutyl)amino-4-(3-[4-{4-phenoxybutoxy}-phenyl]-1-thiapropyl)phenyl-N-phenylsulfonylbenzamide

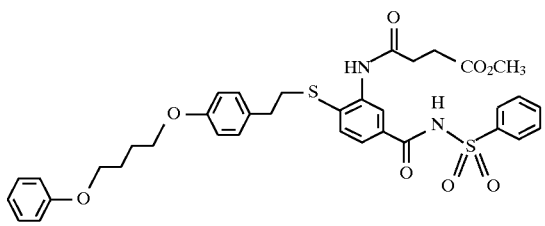

The product of Example 32c (0.28 g), benzenesulfonamide (0.07 g), 3-dimethylaminopropylcarbodiimide (0.1 g) and 4-dimethylaminopyridine (0.08 g) were stirred together for 18 h in dichloromethane (5 ml). The mixture was poured into water and the organic phase purified by preparative TLC, then recrystallised from ethyl acetate and heptane to give a white powder (0.08 g) m.p. 188°–190° C.

$^1$H-NMR (CDCl$_3$) δ: 1.8–2.0 (4H,m), 2.6–3.0 (4H,m), 3.55 (3H,s), 4.0–4.2 (4H,m), 5.5–6.0 (1H,br), 6.8–7.6 (14H, m), 8.0–8.2 (8H,m), 8.5 (1H,br).

HPLC $T_R$: 4.3 min, 70:30 0.1.

b) 3-([4-carboxy-1-oxobutyl)amino-4-(3-[4-{4-phenoxybutoxy}phenyl]-1-thiapropyl)phenyl)-N-phenylsulfonylbenzamide

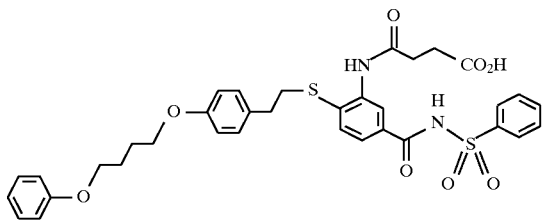

This was prepared from the product of Example 35b, following the procedure of Example 32d, as white solid (0.07 g) m.p. 158°–160° C.

HPLC $T_R$: 2.9 min, 70:30:0.1.

Example 36

5-aza-6-(5-carboxy-2-(3-[3-{4-phenoxybutoxy}phenyl]propoxy)phenyl)-6-oxohexanoic acid

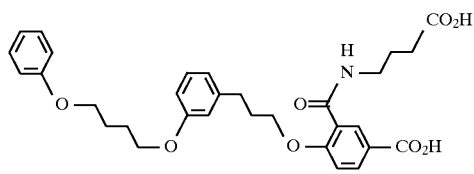

This was prepared from 3-[3-{4-phenoxybutoxy}phenyl] propyl bromide and the product of Example 4a following the procedure of Examples 4b and 4c.

HPLC $T_R$: 4.1 min, 70:30:01.

Ester: $^1$H-NMR (CDCl$_3$) δ: 1.8–2.2 (8H,m), 2.3 (2H,t) 2.75 (2H,t), 3.45 (2H,t), 3.56 (3H,s), 3.8–4.3 (6H,m), 6.7–7.4 (10H,m), 7,8 (1H,m), 8.10 (1H,dd), 8.70 (1H,d).

We claim:

1. Benzoic acid derivatives of the formula (I)

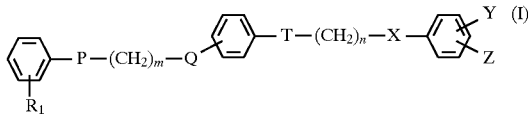

where

R$^1$ represents hydrogen, alkyl having up to 6 carbon atoms or represents substituted phenyl, P and Q each represent oxygen, sulfur or a bond, X represents oxygen, sulfur or —CONH—, T represents an ethylene group, oxygen, sulfur or a bond, Y represents a group —COOH, —NHSO$_2$R$^3$ or —CONHSO$_2$R$^3$ wherein R$^2$ denotes hydrogen, halogen, trifluoromethyl, trifluoromethoxy, nitro, cyano or denotes alkyl or alkoxy, and Z represents a group of the formula —COOH, COR$^4$, —CO(CH$_2$)$_p$CO$_2$H, —O(CH$_2$)$_p$Co$_2$H, —S(CH$_2$)$_p$CO$_2$H, NO$_2$, —CONHWCO$_2$H or —NHWCO$_2$H wherein R$^2$ has the above mentioned meaning, R$^3$ denotes trifluoromethyl, alkyl or optionally substituted phenyl, R$^4$ represents a group of the formula WCO$_2$H or alkyl, p is an integer from 0 to 5 and W denotes phenylene, an alkylene group having up to 8 carbon atoms, which is optionally substituted by alkyl or cycloalkyl each having up to 6 carbon atoms or denotes a group —CO(CH$_2$)$_q$— or —(CH$_2$)$_q$— where q is an integer from 0 to 5 m is an integer from 0 to 6 and n is an integer from 0 to 4 and salts thereof, with the proviso that if R$^1$ represents hydrogen, P is a bond, m is 0, Q is a bond, T is a bond, n is 0, X is oxygen, and Y is p-COOH, then Z is not m-NO$_2$ or m-COOH.

2. Benzoic acid derivatives of the formula according to claim 1, wherein

R$_1$ represents hydrogen,

P and Q represent oxygen,

X represents oxygen sulfur or —NH—,

T represents a bond,

Y represents a group —COOH and/or

Z has the abovementioned meaning m represents an integer H and their salts.

3. Benzoic acid derivatives of the formula according to claim 1, wherein

R$_1$ represents hydrogen,

P and Q represent oxygen,

T represents a bond,

X represents oxygen,

Y represents a group —COOH, m is an integer 4, n is an integer 3 and

Z represents a group —CONH(CH$_2$)$_q$CO$_2$H, —NHCO(CH$_2$)$_q$CO$_2$H or —CONHC$_6$H$_4$CO$_2$H where q is an integer 0 to 5 and salts thereof.

4. Benzoic acid derivatives of the formula (Ib)

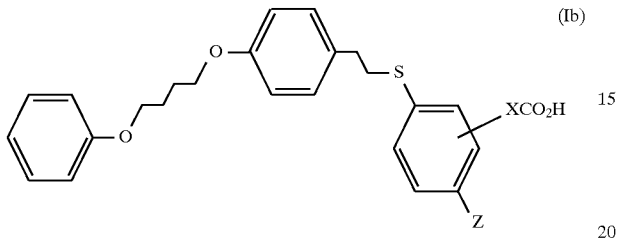

(Ib)

wherein

X represents CONH(CH$_2$)$_q$, NHCO(CH$_2$)$_q$ or O(CH$_2$)$_q$ and

Z represents carboxylic acid, NHSO$_2$R$^2$ or CONHSO$_2$R$^2$, where

R$_2$ represents C$_1$–C$_4$-alkyl or phenyl, and q is an integer 1 to 5 and salts thereof.

5. Benzoic acid derivatives according to claim 1 wherein such compound is 5-aza-6-(5-carboxy-2-[3-{4-phenoxybutoxy}phenylpropoxy]-6-oxohexanoic acid of the formula

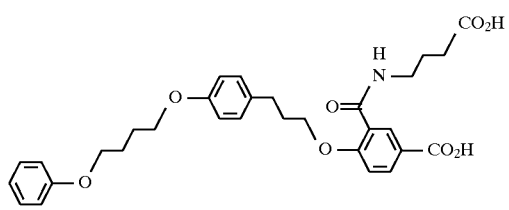

and salts thereof.

6. Benzoic acid derivatives according to claim 1 wherein such compound is 5-carboxy-2-[([3-{4-phenoxybutoxy}-phenyl]-1-oxopropyl)amino]phenoxyacetic acid of the formula

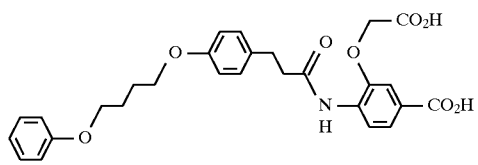

and salts thereof.

7. Benzoic acid derivatives according to claim 1 wherein such compound is 5-carboxy-2-[([3-{4-phenoxybutoxy}-phenyl]-1-oxopropyl)amino]phenyl-5-oxopentanoic acid of the formula

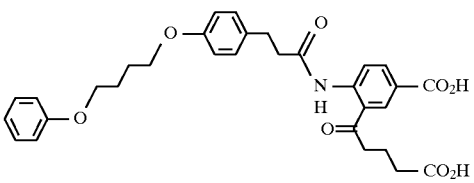

and salts thereof.

8. Benzoic acid derivatives according to claim 1 wherein such compound is 2-(3-[4-{4-phenoxybutoxy}phenyl]propoxy)-5-(methylsulfonylamino)-benzoic acid of the formula

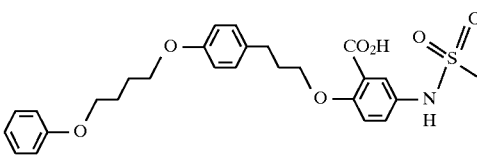

and salts thereof.

9. Benzoic acid derivatives according to claim 1 wherein such compound is methyl 4-aza-5-([5-(methanesulfonyl)amino-2-(3-[4-{4-phenoxybutoxy}-phenyl]propoxy)-phenyl)-5-oxopentanoate of the formula

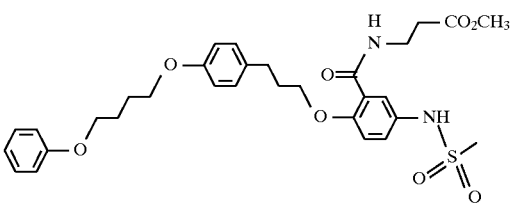

and salts thereof.

10. Benzoic acid derivatives according to claim 1 wherein such compound is 3-([4-carboxy-1-oxobutyl)amino-4-(3-[4-{4-phenoxybutoxy}phenyl]-1-thiapropyl)phenyl)-N-phenylsulfonylbenzamide of the formula

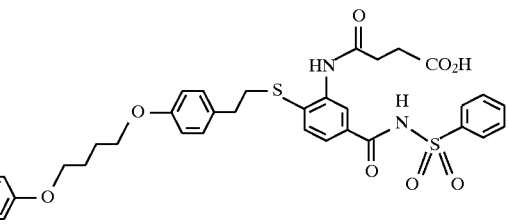

and salts thereof.

11. A composition for the treatment of respiratory diseases comprising amount effective therefore of a compound or salt thereof according to claim 1 and a pharmacologically acceptable diluent.

12. The method of treating respiratory diseases in a patient in need thereof which comprises administering to such patient an amount effective there-fore of a compound or salt thereof according to claim 1.

* * * * *